US012409199B2

(12) United States Patent
Capano et al.

(10) Patent No.: US 12,409,199 B2
(45) Date of Patent: Sep. 9, 2025

(54) METHODS OF TREATING ENDOMETRIOSIS AND OTHER NONCANCER GYNECOLOGICAL DISORDERS WITH HEMP EXTRACT

(71) Applicants: Ecofibre USA Inc., Georgetown, KY (US); The University of Newcastle, Callaghan (AU)

(72) Inventors: Alexandra M. Capano, Philadelphia, PA (US); Pradeep Singh Tanwar, Fletcher (AU); Alex Nance, Georgetown, KY (US)

(73) Assignees: Ecofibre USA Inc., Georgetown, KY (US); The University of Newcastle, Callaghan (AU)

( * ) Notice: Subject to any disclaimer, the term of this patent is extended or adjusted under 35 U.S.C. 154(b) by 0 days.

(21) Appl. No.: 18/639,285

(22) Filed: Apr. 18, 2024

(65) Prior Publication Data
US 2024/0261355 A1   Aug. 8, 2024

Related U.S. Application Data

(62) Division of application No. 18/299,810, filed on Apr. 13, 2023, now Pat. No. 11,986,505, which is a division of application No. 18/050,023, filed on Oct. 26, 2022, now Pat. No. 11,654,172.

(60) Provisional application No. 63/263,022, filed on Oct. 26, 2021, provisional application No. 63/263,020, filed on Oct. 26, 2021, provisional application No. 63/263,026, filed on Oct. 26, 2021.

(51) Int. Cl.
*A61K 36/00* (2006.01)
*A61K 31/015* (2006.01)
*A61K 31/045* (2006.01)
*A61K 31/05* (2006.01)
*A61K 31/352* (2006.01)
*A61K 31/353* (2006.01)
*A61K 31/60* (2006.01)
*A61K 36/185* (2006.01)
*A61P 35/00* (2006.01)

(52) U.S. Cl.
CPC .......... *A61K 36/185* (2013.01); *A61K 31/015* (2013.01); *A61K 31/045* (2013.01); *A61K 31/05* (2013.01); *A61K 31/352* (2013.01); *A61K 31/353* (2013.01); *A61K 31/60* (2013.01); *A61P 35/00* (2018.01)

(58) Field of Classification Search
CPC ...................................................... A61P 35/00
See application file for complete search history.

(56) References Cited

U.S. PATENT DOCUMENTS

| 10,098,867 | B2 | 10/2018 | Javid et al. |
| 11,123,308 | B2 | 9/2021 | Yu et al. |
| 2010/0273895 | A1 | 10/2010 | Stinchcomb et al. |
| 2011/0086113 | A1 | 4/2011 | Velasco Diez et al. |
| 2015/0086653 | A1 | 3/2015 | Parolaro et al. |
| 2016/0136128 | A1 | 5/2016 | Javid et al. |
| 2019/0282513 | A1 | 9/2019 | Yerike |
| 2020/0253919 | A1 | 8/2020 | Raz et al. |
| 2020/0408740 | A1 | 12/2020 | Ballan et al. |
| 2021/0052512 | A1 | 2/2021 | Guy et al. |
| 2021/0068444 | A1 | 3/2021 | Alarcon et al. |
| 2021/0069608 | A1 | 3/2021 | Galyuk |
| 2021/0085638 | A1 | 3/2021 | Hospodor |
| 2021/0128521 | A1 | 5/2021 | Palaio |
| 2021/0145764 | A1 | 5/2021 | Lephart |
| 2022/0000774 | A1 | 1/2022 | Dely |
| 2022/0054429 | A1 | 2/2022 | Nathan et al. |
| 2022/0062224 | A1 | 3/2022 | Gubler et al. |
| 2022/0193164 | A1 | 6/2022 | White |
| 2022/0202765 | A1 | 6/2022 | Altman et al. |
| 2022/0248619 | A1 | 8/2022 | Kleidon |
| 2022/0253919 | A1 | 8/2022 | Denner |
| 2022/0331287 | A1 | 10/2022 | Morgan et al. |
| 2023/0015268 | A1 | 1/2023 | Altman et al. |
| 2023/0127098 | A1 | 4/2023 | Capano et al. |
| 2023/0132189 | A1 | 4/2023 | Capano et al. |
| 2023/0248747 | A1 | 8/2023 | Altman et al. |
| 2023/0355645 | A1 | 11/2023 | Storch et al. |

FOREIGN PATENT DOCUMENTS

| CN | 108433880 A | 8/2018 |
| CN | 110063953 A | 7/2019 |
| EP | 3368024 A1 | 9/2018 |
| EP | 3449992 A1 | 3/2019 |
| EP | 3544598 A1 | 10/2019 |
| EP | 3915550 A1 | 12/2021 |
| EP | 3937914 A1 | 1/2022 |

(Continued)

OTHER PUBLICATIONS

Marinotti et al, Differentiating Full-Spectrum Hemp Extracts from CBD Isolates: Implications for Policy, Safety and Science. Journal of Dietary Supplements, (Sep. 2, 2020) vol. 17, No. 5, Sp. Iss. SI.). (Year: 2020).*

(Continued)

*Primary Examiner* — Qiuwen Mi
(74) *Attorney, Agent, or Firm* — Vos-IP, LLC

(57) ABSTRACT

A method for treating a noncancerous gynecological disorder comprising: administering to a patient an effective amount of composition comprising a *cannabis* extract comprising cannabidiol (CBD) wherein the composition is preferably administered in a mucosal form, such as intravaginally.

11 Claims, 17 Drawing Sheets

(56) References Cited

FOREIGN PATENT DOCUMENTS

| | | | |
|---|---|---|---|
| GB | 2516335 A | 1/2015 | |
| RU | 2745687 C1 * | 3/2021 | ............ A61K 31/05 |
| WO | WO/2013/165251 A1 | 11/2013 | |
| WO | WO/2014/057067 A1 | 4/2014 | |
| WO | WO/2016/187679 A1 | 12/2016 | |
| WO | WO/2017/072773 A1 | 5/2017 | |
| WO | WO/2018/167038 A1 | 9/2018 | |
| WO | WO/2019/003163 A2 | 1/2019 | |
| WO | WO/2019/034113 A1 | 2/2019 | |
| WO | WO-2019003163 A3 * | 3/2019 | ............ A61K 31/01 |
| WO | WO/2019/106652 A1 | 6/2019 | |
| WO | WO/2019/145552 A1 | 8/2019 | |
| WO | WO/2019/195943 A1 | 10/2019 | |
| WO | WO/2019/222459 A1 | 11/2019 | |
| WO | WO/2020/036655 A9 | 2/2020 | |
| WO | WO/2020/163775 A1 | 8/2020 | |
| WO | WO/2020/165878 A1 | 8/2020 | |
| WO | WO/2020/183455 A1 | 9/2020 | |
| WO | WO/2020/194237 A1 | 10/2020 | |
| WO | WO/2020/209902 A1 | 10/2020 | |
| WO | WO/2021/011790 A1 | 1/2021 | |
| WO | WO/2021/016718 A1 | 2/2021 | |
| WO | WO/2021/028646 A1 | 2/2021 | |
| WO | WO/2021/099792 A1 | 5/2021 | |
| WO | WO/2021/130728 A1 | 7/2021 | |
| WO | WO/2021/158251 A1 | 8/2021 | |
| WO | WO/2021/235977 A1 | 11/2021 | |
| WO | WO/2021/240510 A1 | 12/2021 | |
| WO | WO/2021/245522 A1 | 12/2021 | |
| WO | WO/2022/013854 A1 | 1/2022 | |
| WO | WO/2022/016160 A1 | 1/2022 | |
| WO | WO/2022/018708 A1 | 1/2022 | |
| WO | WO/2022/105952 A1 | 5/2022 | |
| WO | WO/2022/118303 A1 | 6/2022 | |
| WO | WO/2022/144878 A1 | 7/2022 | |
| WO | WO/2022/165349 A1 | 8/2022 | |
| WO | WO/2022/165439 A1 | 8/2022 | |
| WO | WO/2022/201043 A1 | 9/2022 | |
| WO | WO/2022/215071 A1 | 10/2022 | |
| WO | WO/2022/225658 A1 | 10/2022 | |
| WO | WO/2023/287742 A1 | 1/2023 | |
| WO | WO/2023/014818 A2 | 2/2023 | |
| WO | WO/2023/062634 A1 | 4/2023 | |

OTHER PUBLICATIONS

International Search Report issued in International Application No. PCT/US2022/078698 dated Dec. 14, 2022.
International Search Report issued in International Application No. PCT/US2022/078701 dated Feb. 15, 2023.
International Search Report issued in International Application No. PCT/US2022/078691 dated Jan. 30, 2023.
International Search Report issued in International Application No. PCT/US2022/078693 dated Jan. 30, 2023.
Armour, et al., "Self-Management Strategies Amongst Australian Women With Endometriosis: A National Online Survey", BMC Complementary and Alternative Medicine, vol. 19, No. 1, art. 17, Jan. 15, 2019, 1-8.
Escudero-Lara, et al., "Disease-Modifying Effects of Natural $\Delta^9$-Tetrahydrocannabinol in Endometriosis-Associated Pain", eLife, vol. 9, art. e50356, Jan. 14, 2020, https://elifesciences.org/articles/50356.
Fonseca, et al., "Cannabinoid-Induced Cell Death in Endometrial Cancer Cells: Involvement of TRPV1 Receptors in Apoptosis", Journal of Physiology and Biochemistry, vol. 74, No. 2, Feb. 13, 2018, 261-272.
Fraguas-Sánchez, et al., "Enhancing Ovarian Cancer Conventional Chemotherapy Through the Combination With Cannabidiol Loaded Microparticles", European Journal of Pharmaceutics and Biopharmaceutics, vol. 154, Jul. 17, 2020, 246-258.
Go, et al., "Cannabidiol Enhances Cytotoxicity of Anti-Cancer Drugs in Human Head and Neck Squamous Cell Carcinoma", Scientific Reports, vol. 10, No. 1, art. 20622, Nov. 26, 2020, 1-11.
Griffiths, et al., "Cannabidiol Suppresses 3-Dimensional Ovarian Cancer Growth and May Enhance Potency of Classic and Epigenetic Therapies", Gynecologic Oncology, vol. 162, suppl. 1, Abstracts for the 2021 Society of Gynecologic Oncology 52nd Annual Meeting on Women's Cancer, Aug. 18, 2021, S102-S103.
Hazekamp, et al., "Preparative Isolation of Cannabinoids from Cannabis sativa by Centrifugal Partition Chromatography", Journal of Liquid Chromatography & Related Technologies, vol. 27, No. 15, 2004, 2421-2439.
Jaidee, et al., "Kinetics of Cbd, $\Delta^9$-THC Degradation and Cannabinol Formation in Cannabis Resin at Various Temperature and pH Conditions", Cannabis and Cannabinoid Research, vol. 7, No. 4, Aug. 9, 2022, 1-11.
Jin, et al., "Identification of Chemotypic Markers in Three Chemotype Categories of Cannabis Using Secondary Metabolites Profiled in Inflorescences, Leaves, Stem Bark, and Roots", Frontiers in Plant Science, vol. 12, art. 699530, Jul. 1, 2021, 1-16.
Kenyon, et al., "Report of Objective Clinical Responses of Cancer Patients to Pharmaceutical-Grade Synthetic Cannabidiol", Anticancer Research, vol. 38, No. 10, Oct. 1, 2018, 5831-5835.
Lazarjani, et al., "Processing and Extraction Methods of Medicinal Cannabis: A Narrative Review", Journal of Cannabis Research, vol. 3, art. 32, Jul. 19, 2021, 1-15.
Marinelli, et al., "The Effects of Cannabidiol and Prognostic Role of TRPV2 in Human Endometrial Cancer", International Journal of Molecular Sciences, vol. 21, No. 15, art. 5409, Jul. 29, 2020, 1-22.
Marinotti, et al., "Differentiating Full-Spectrum Hemp Extracts from CBD Isolates: Implications for Policy, Safety and Science", Journal of Dietary Supplements, vol. 17, No. 5, Jun. 16, 2020, 517-526.
Midatech Pharma US Inc., Soltamox® Product Label, Revised Apr. 2019.
Ökten, et al., "Cannabidiol as a Potential Novel Treatment for Endometriosis by Its Anti-Inflammatory and Anti-Oxidative Effects in an Experimental Rat Model", Human Reproduction, vol. 37, issue supp. 1, Jun. 30, 2022, i111.
Olivas-Aguirre, et al., "Tamoxifen Sensitizes Acute Lymphoblastic Leukemia Cells to Cannabidiol by Targeting Cyclophilin-D and Altering Mitochondrial $Ca^2$ Homeostasis", International Journal of Molecular Sciences, vol. 22, No. 16, Aug. 13, 2021, 1-14.
Rais, et al., "Phytochemicals in the Treatment of Ovarian Cancer", Frontiers in Bioscience-Elite, vol. 9, No. 1, Jan. 1, 2017, 67-75.
Rush, et al., "Cannabidiol: Assessing Activity in Ovarian and Endometrial Carcinoma Cell Lines", Abstracts for the 2021 Society of Gynecologic Oncology 52nd Annual Meeting on Women's Cancer, Featured Posters 188—Poster Session, vol. 162, suppl. 1, Aug. 1, 2021, https://doi.org/10.1016/S0090-8258(21)00839-8.
Sumanasekera, et al., "Hemp Extract With Specific Anti-Cancer Properties Against Ovarian Cancer", The FASEB Journal Special Issue: Experimental Biology 2021 Meeting Abstracts, vol. 35, No. S1, May 14, 2021, https://doi.org/10.1096/fasebj.2021.35.S1.02877.
Van Weelden, et al., "Anti-Estrogen Treatment in Endometrial Cancer: A Systematic Review", Frontiers in Oncology, vol. 9, art. 359, May 7, 2019, 1-12.
Boretto, et al., "Patient-Derived Organoids From Endometrial Disease Capture Clinical Heterogeneity and Are Amenable to Drug Screening", Nature Cell Biology, vol. 21, Aug. 1, 2019, 1041-1051.
Fraguas-Sánchez, Ana I., et al., "PLGA Nanoparticles for the Intraperitoneal Administration of CBD in the Treatment of Ovarian Cancer: In Vitro and In Ovo Assessment", Pharmaceutics, vol. 12, No. 5, art. 439, May 9, 2020, 1-19.

* cited by examiner

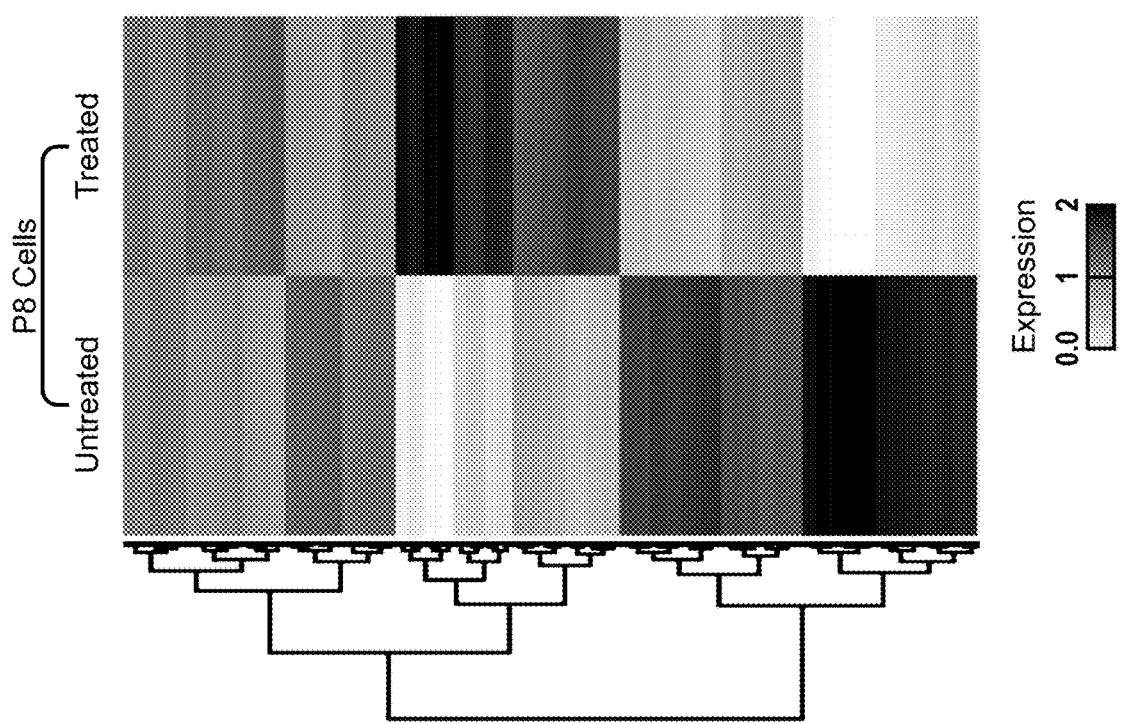
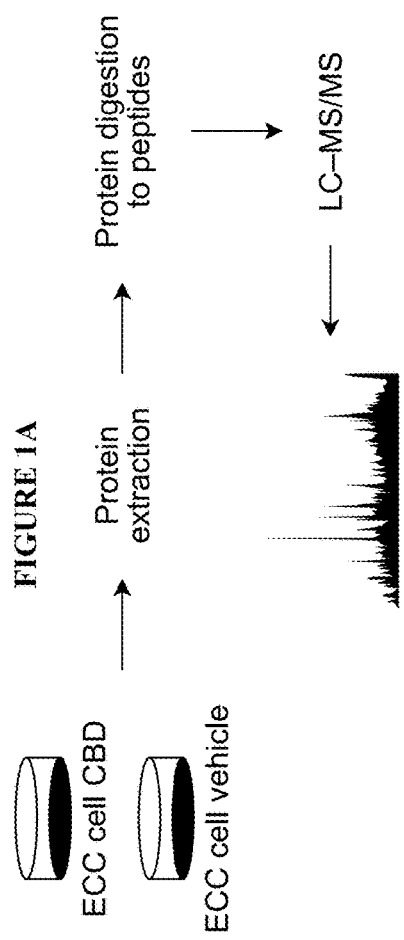
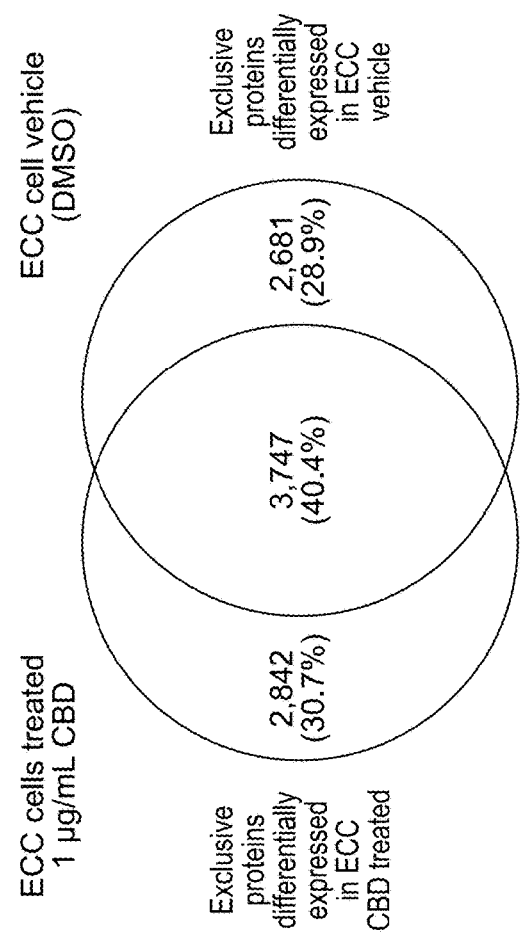

Cannabinoid Receptor 2 Protein Expression in Endometrial Cancer Patient Samples

Endometrial Cancer (Endometrioid Type)

Cannabinoid Receptor 1 Protein Expression in Endometrial Cancer Patient Samples

Endometrial Cancer (Endometrioid Type)

Endometriosis

4× images, scale bar 250 µm

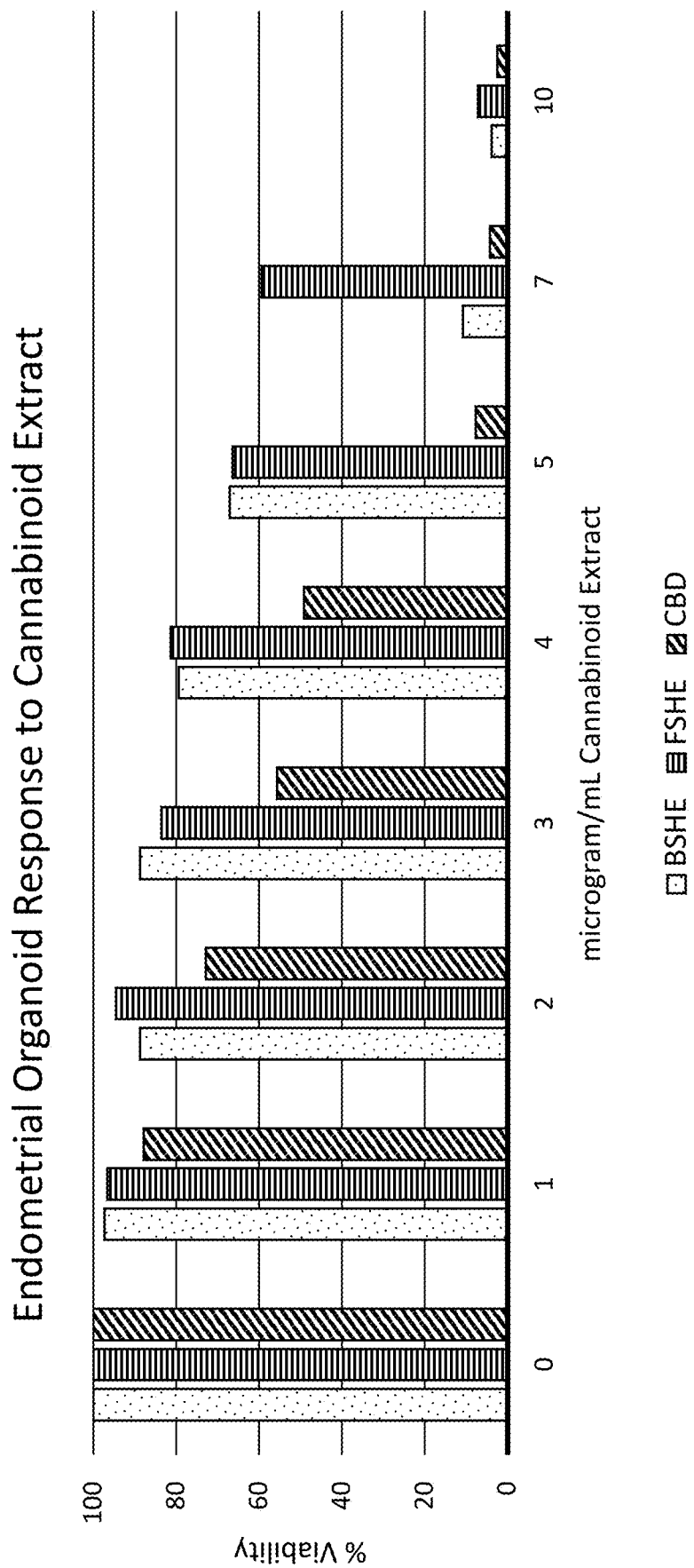

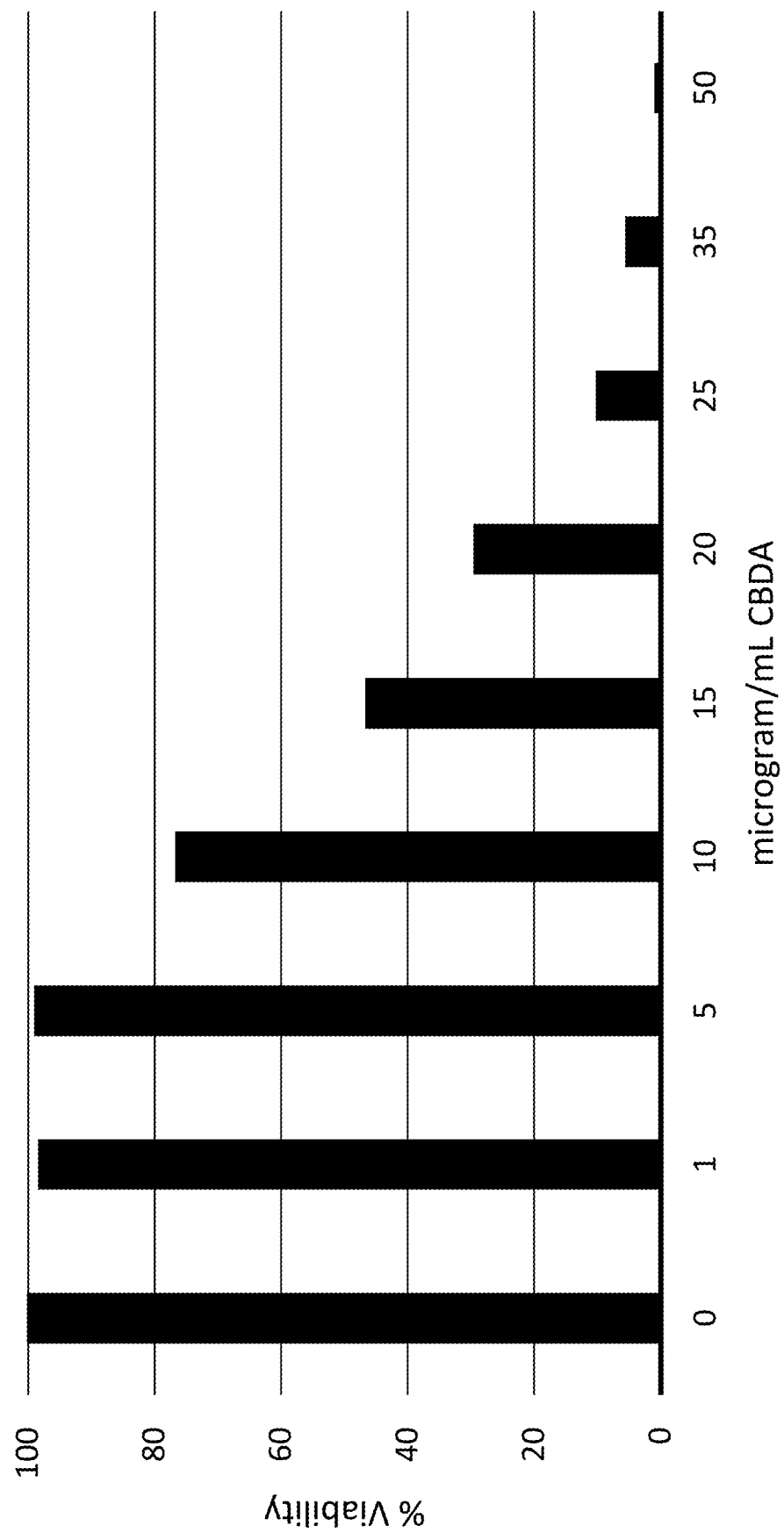

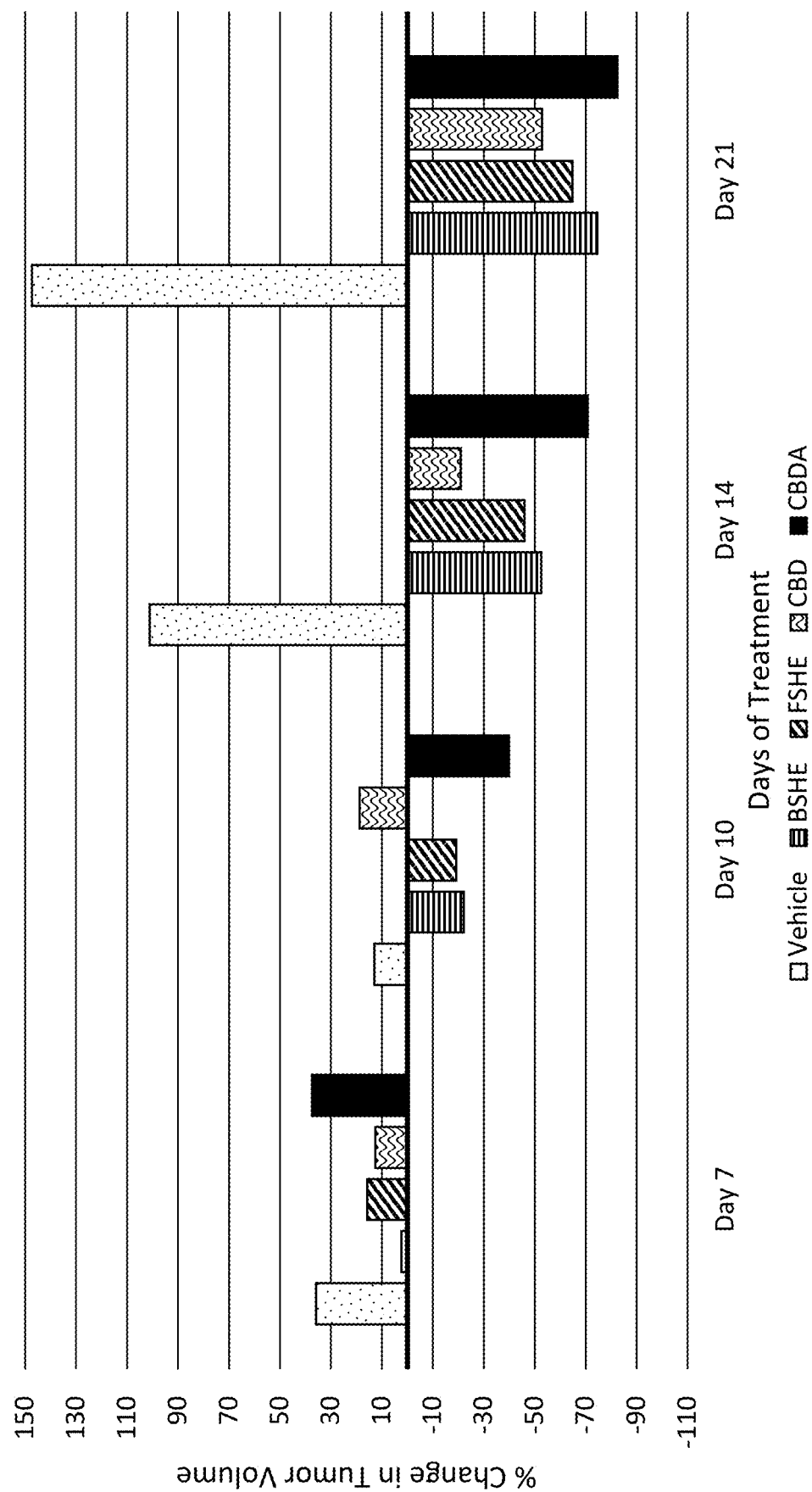

Effects pH and Cannabinoid Extract (10 μg/mL) on Ovarian Cancer Organoid Viability

METHODS OF TREATING ENDOMETRIOSIS AND OTHER NONCANCER GYNECOLOGICAL DISORDERS WITH HEMP EXTRACT

CROSS-REFERENCE TO RELATED APPLICATIONS

This application is a divisional of U.S. patent application Ser. No. 18/299,810 filed on Apr. 13, 2023, which is a divisional of U.S. patent application Ser. No. 18/050,023 filed on Oct. 26, 2022, which claims the benefit of U.S. Provisional Patent Application No. 63/263,026 filed on Oct. 26, 2021, U.S. Provisional Patent Application No. 63/263,020 filed on Oct. 26, 2021, and U.S. Provisional Patent Application No. 63/263,022 filed on Oct. 26, 2021, with the United States Patent and Trademark Office, the contents of which are incorporated herein by reference in their entirety.

FIELD OF THE INVENTION

The inventions disclosed herein are related to compositions and therapeutic treatments of endometriosis and other noncancerous gynecological disorders, through administration of an effective amount of *cannabis* extracts alone or in combination with a second therapeutic agent. The *cannabis* extracts comprise one or more cannabinoids, and specifically therapeutic amounts of cannabidiol (CBD) and often include one or more additional cannabinoid, terpene, or other molecules within the *cannabis* extract.

BACKGROUND OF THE INVENTION

Women face a host of noncancerous gynecological disorders for which there is currently no adequate method of treatment. These conditions include painful non-life-threatening disorders such as fibroids, polycystic ovarian syndrome, ovarian cysts, adhesions, pelvic masses, pelvic infection, endometriosis, dysmenorrhea, and others (collectively "noncancerous gynecological cancers"). Many of these disorders are more than just a nuisance and often cause significant pain and suffering.

Various forms of pelvic pain, including dysmenorrhea and endometriosis, affect over 80% of women. Global studies report to over 30% of women experience pelvic pain severe enough to miss school or work, and up to 80% of women report loss of productivity due to associated symptoms. The disruption is not limited to days of menstruation, as chronic pelvic pain prevalence, characterized as three to six months in duration, affects 24% of women. The negative consequences of pelvic pain are significant and include absenteeism's socioeconomic impacts, lower quality of life, and increased reports of anxiety, sleep disturbances, and other mood disorders. Analgesic use is reported by 80-93% of women with pelvic pain, with varying frequency. Combined, 47% report using pain medication "always" or "often." Studies report abusive or inappropriate use of both NSAIDs and narcotic pain medications, such as opioids, further increasing health risks of pelvic pain.

Endometriosis, a disorder in which tissue that normally lines the uterus grows outside the uterus, is a common gynecological condition affecting an estimated 6 to 10 percent of American women of childbearing age. Current treatment plans for endometriosis include: monitoring the course of the disease which provides no relief for the woman; prescribing pain medications and anti-inflammatory drugs which eases the symptoms associated with endometriosis but does not treat the underlying cause of the disease; hormone therapy which may have undesirable side-effects for the woman; non-invasive surgery such as laparoscopy or laparotomy but the relief from these surgical procedures is not permanent and symptoms may return after surgery; or hysterectomy which is highly evasive and would prevent the woman from bearing future children. Even under the best of circumstances, many of the treatment options remain wholly inadequate. Clearly, none of the current treatment options available to women diagnosed with endometriosis provide long lasting relief from the disorder without taking drastic action that may render the woman infertile.

Women diagnosed with severe dysmenorrhea, painful menstrual periods which are caused by uterine contractions, may be prevented from doing their normal daily activities for several days out of each month. For some women, severe pain comes with other symptoms, including diarrhea, nausea, vomiting, headache, and dizziness. Currently there are options for managing the symptoms of dysmenorrhea such as taking pain relief medications or non-steroidal anti-inflammatory drugs, resting, changing one's diet or increasing exercise. There are also invasive procedures such as endometrial ablation, a procedure to destroy the lining of the uterus, endometrial resection, a procedure to remove the lining of the uterus and hysterectomy, the surgical removal of the uterus. The non-invasive measures for managing the symptoms of dysmenorrhea do not treat the condition itself and surgical procedures are highly invasive and may create fertility problems for women of childbearing age.

Fibroids, a common condition diagnosed in over 200,000 women per year, are noncancerous growths of the uterus. Fibroids can cause discomfort and may lead to complications such as a drop in red blood cells (anemia), which causes fatigue, from heavy blood loss. Current treatment plans for fibroids are similar to those discussed above-watchful waiting, nonsteroidal anti-inflammatory drugs, hormonal therapy, surgical removal or hysterectomy.

Treatment for noncancerous gynecological disorders remains inadequate. Applicant has identified that therapeutic levels of *cannabis* extracts comprising CBD are effective in treating endometriosis and other noncancerous gynecological disorders. In certain embodiments, these *cannabis* extracts are provided in dosing forms such as oral, oral mucosal, intravaginal, and combinations thereof. These and other embodiments are detailed with more particularity herein.

SUMMARY OF THE INVENTION

The particular embodiments disclosed herein relate to methods of treating endometriosis and other noncancerous gynecological disorders through intravaginal application of a BSHE or FSHE formulation, which comprises CBD. In particular, the formulation enables intravaginal delivery CBD and other cannabinoids and other terpenes and molecules within the FSHE or BSHE, and are able to relieve symptoms of endometriosis, including of destruction of endometrial cells which are displaced and present inappropriately outside of the uterus.

In a further embodiment, a method for treating endometriosis comprising: administering to a patient an effective amount of an intravaginal composition comprising a full spectrum hemp extract (FSHE) or a broad spectrum hemp extract (BSHE) comprising cannabidiol (CBD).

In a further preferred embodiment, the method wherein the endometriosis is an ovarian endometrioma or a deep endometriosis.

In a further embodiment, a method of treatment of dysmenorrhea or fibroids comprising: administering to a patient an effective amount of an intravaginal composition comprising a full spectrum hemp extract (FSHE) or a broad spectrum hemp extract (BSHE) comprising cannabidiol (CBD).

In a further preferred embodiment of the preceding method, use, or therapeutic further comprising a hormonal therapy, a Gn-RH therapy, a progestin therapy, an aromatase inhibitor, or combinations thereof.

In an embodiment, the present invention provides a *cannabis* extract for use in a method of treating a noncancerous gynecological disorder (NCGD) in a patient, wherein said *cannabis* extract comprises cannabidiol (CBD) and wherein said method is a method for concurrently treating endometrial cancer and endometriosis, and the method comprises administering the *cannabis* extract to the patient concomitantly via an oral formulation and via an intravaginal formulation. As defined herein, the term "concomitantly" means that the oral formulation and the intravaginal formulation are administered to the patient no more than 72 hours apart, preferably no more than 48 hours apart, and more preferably no more than 24 hours apart, for example no more than 12 hours apart, no more than 6 hours apart, no more than 4 hours, apart, no more than 3 hours apart, no more than 2 hours apart, no more than an hour apart, no more than 30 minutes apart, or simultaneously. Thus, in an embodiment, the present invention provides an oral formulation for use in a method for concurrently treating endometrial cancer and endometriosis, wherein said oral formulation comprises a *cannabis* extract comprising cannabidiol (CBD) and a pharmaceutically acceptable excipient, and said method comprises administration of the oral formulation concomitantly with an intravaginal formulation comprising a *cannabis* extract comprising cannabidiol (CBD) and a pharmaceutically acceptable excipient. In a further embodiment, the present invention provides an intravaginal formulation for use in a method for treating a NCGD, wherein said intravaginal formulation comprises a *cannabis* extract comprising cannabidiol (CBD) and a pharmaceutically acceptable excipient, and said method comprises administration of the intravaginal formulation concomitantly with an oral mucosal formulation comprising a *cannabis* extract comprising cannabidiol (CBD) and a pharmaceutically acceptable excipient.

In an embodiment, the present invention provides a pharmaceutical composition for use in a method of treating a NCGD, wherein said pharmaceutical composition comprises a *cannabis* extract having an effective amount of CBD.

In an embodiment, the present invention provides the use of a *cannabis* extract comprising cannabidiol (CBD) in the manufacture of a medicament for use in a method of treating a NCGD.

In an embodiment, the present invention provides the use of an intravaginal composition comprising a *cannabis* extract comprising cannabidiol, and a pharmaceutically acceptable excipient, in the manufacture of a medicament for use in a method of treating a NCGD.

In an embodiment, the present invention provides the use of a *cannabis* extract comprising cannabidiol (CBD) in the manufacture of a medicament for use in a method of treating a NCGD.

In a preferred embodiment, a method of treatment of a NCGD comprising, administering to a patient via an intravaginal application, an effective amount of a pharmaceutical composition comprising a *cannabis* extract comprising between 1% and 99.9% CBD.

In a further embodiment, the method wherein the effective dose is sufficient to generate a concentration of at least 10 µg/mL of the CBD at the target tissue.

Accordingly, mucosal dosing, particularly intravaginal dosing, has a therapeutic efficacy that can allow for targeted treatment of EC cells, which will treat both localized lesions and internalized tissues. These data were confirmed by further testing within human patients, which showed that treatment with CBD was effective in treating NCGD such as endometriosis, ovarian endometrioma, deep endometriosis, dysmenorrhea, or fibroids.

In a preferred embodiment, a *cannabis* extract for use in a method of treating a noncancerous gynecological disorder (NCGD) in a patient wherein said *cannabis* extract comprises cannabidiol (CBD).

In a further embodiment, the *cannabis* extract for use wherein said *cannabis* extract is selected from a full spectrum hemp extract (FSHE), a broad spectrum hemp extract (BSHE), a CBD isolate, and cannabidiolic acid (CBDA), optionally wherein the BSHE or FSHE comprises (i) from 50% to 99% by weight of CBD and (ii) at least one other cannabinoid selected from $\Delta$-9-tetrahydrocannabinol ($\Delta^9$-THC), tetrahydrocannabinolic acid (THCA), tetrahydrocannabivarin (THCV), $\Delta$-8-tetrahydrocannabinol ($\Delta^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a further embodiment, the *cannabis* extract for use wherein said *cannabis* extract comprises between 10 mg and 4,250 mg CBD per dose.

In a further embodiment, the *cannabis* extract for use wherein: (a) the method comprises administration of the *cannabis* extract to the patient via an oral dose, an oral mucosal dose, an intravaginal dose, or combinations thereof; and/or (b) the method comprises administration of a dose of the *cannabis* extract to the patient at least once every three days, preferably at least once a day, at least twice a day, or at least three times a day; and/or (c) the method comprises administration of an amount of the *cannabis* extract sufficient to generate a concentration of at least 10 µg/mL of the *cannabis* extract at a target tissue in the patient, preferably wherein the target tissue is a noncancerous tissue of a female reproductive tract; and/or (d) the method comprises administration of an amount of the *cannabis* extract sufficient to reach an effective therapeutic level as measured through systemic plasma levels of CBD; and/or (e) the method comprises administration of between 20 mg and 4,250 mg of CBD to the patient per day; and/or (f) the *cannabis* extract is formulated at an acidic pH, preferably at a pH between 3.5 and 6.

In a further embodiment, the *cannabis* extract for use wherein: (a) the NCGD is endometriosis; and/or (b) the NCGD is dysmenorrheal and/or (c) the NCGD is fibroids.

In a further embodiment, the *cannabis* extract for use wherein said *cannabis* extract comprises between 1% and 99.9% CBD and wherein the method comprises administering the *cannabis* extract to the patient via intravaginal administration, preferably wherein: (a) the *cannabis* extract comprises between 60% and 99.9% CBD; and/or (b) the *cannabis* extract is selected from a full spectrum hemp extract (FSHE), a broad spectrum hemp extract (BSHE), and a CBD isolate; and/or (c) the *cannabis* extract comprises CBDA.

In a preferred embodiment, a mucosal composition for use in a method of treating a noncancerous gynecological disorder (NCGD) in a patient wherein said mucosal composition comprises a *cannabis* extract and a pharmaceutically acceptable excipient.

In a further embodiment, the mucosal composition for use wherein the composition comprises (i) an oil or fat as a carrier and/or (ii) at least one terpene, at least one polyphenol, at least one essential fatty acid, at least one phytonutrient, or a combination thereof, optionally wherein the at least one terpene, at least one polyphenol, at least one essential fatty acid, at least one phytonutrient, or combination thereof make up between 1% and 50% by weight of the total weight of the composition, further optionally wherein: the terpene is selected from β-myrcene, β-caryophyllene, linalool, α-pinene, citral, D-limonene, eucalyptol, and combinations thereof; and/or the polyphenol is selected from a catechin, quercetin, cannflavin A/B/C, rutin, chlorogenic acid, and combinations thereof; and/or the essential fatty acid is selected from an omega 3 acid, an omega 6 acid, an omega 9 acid, and combinations thereof; and/or the phytonutrient is selected from a tocopherol, a sterol, carotene, an aliphatic alcohol, a mineral, and combinations thereof.

In a further embodiment, the mucosal composition for use wherein: (a) the mucosal composition comprises a dose of between 25 mg and 4,250 mg CBD and the method comprises administering the composition to the patient via insertion to a mucosal surface selected from oral mucosa, rectum, vagina, or nasal passages; and/or (b) the method comprises administering at least two doses of the mucosal composition to the patient per day wherein each dose of the mucosal composition comprises between 10 mg and 2,125 mg *cannabis* extract; and/or (c) the mucosal composition has an acidic pH, preferably a pH between 3.5 and 6.

In a further embodiment, the *cannabis* extract for use wherein said method is a method for treating an NCGD and the method comprises administering the *cannabis* extract to the patient concomitantly via a mucosal formulation, preferably wherein the *cannabis* extract is a full spectrum hemp extract (FSHE) or a broad spectrum hemp extract (BSHE).

In a further embodiment, the *cannabis* extract for use wherein said method comprises coadministering to a patient an effective amount of said *cannabis* extract and an effective amount of a second therapeutic agent.

In a preferred embodiment, a pharmaceutical composition for use in a method of treating a noncancerous gynecological disorder (NCGD) wherein said pharmaceutical composition comprises a *cannabis* extract comprising an effective amount of CBD.

In a further embodiment, the pharmaceutical composition for use wherein the composition further comprises: (a) a carrier; and/or (b) at least one additional cannabinoid selected from Δ$^9$-THC, THCA, THCV, Δ$^8$-THC, CBC, CBCA, CBG, CBGA, CBDA, CBDV, CBN, CBL, and combinations thereof; and/or (c) at least one terpene, preferably wherein the terpene is selected from β-myrcene, β-caryophyllene, linalool, α-pinene, citral, D-limonene, eucalyptol, and combinations thereof; and/or (d) at least one polyphenol, preferably wherein the polyphenol is selected from a catechin, quercetin, cannflavin A/B/C, rutin, chlorogenic acid, and combinations thereof; and/or (e) an essential fatty acid, preferably wherein the essential fatty acid is selected from an omega 3 acid, an omega 6 acid, an omega 9 acid, and combinations thereof; and/or (f) a phytonutrient, preferably wherein the phytonutrient is selected from a tocopherol, a sterol, carotene, an aliphatic alcohol, a mineral, and combinations thereof.

In a preferred embodiment, a method for treating a noncancerous gynecological disorder (NCGD) comprising administering to a patient an effective amount of a composition comprising a *cannabis* extract (CE).

In a further embodiment, the method wherein the CE comprises between 50% and 99.9% cannabidiol (CBD).

In a further embodiment, the method wherein the CE is selected from the group consisting of: a full spectrum hemp extract (FSHE), a broad spectrum hemp extract (BSHE), a CBD isolate, and a cannabidiolic acid (CBDA) isolate.

In a further embodiment, the method wherein the CE is administered via an oral form, oral mucosal form, intravaginal form, nasal mucosal form, rectal form, injectable form, and combinations thereof.

In a further embodiment, the method wherein the effective amount of the *cannabis* extract comprising CBD comprises between 10 mg and 4,250 mg of CBD per day. In a further embodiment, the method wherein administration of the CE is a dose given at least once a day, at least twice a day, or at least three times a day.

In a further embodiment, the method wherein the NCGD is an ovarian endometrioma, a deep endometriosis, dysmenorrhea, or a fibroid.

In a further embodiment, the method wherein the CE comprises CBDA at a concentration of between 0.1% and 10%.

In a further embodiment, the method wherein the CE is a BSHE or FSHE and wherein each of the BSHE or FSHE comprises 50% to 99% by weight of CBD and at least one other cannabinoid at a concentration of 0.1% to 10%, selected from the group consisting of: Δ$^9$-THC, THCA, THCV, Δ$^8$-THC, CBC, CBCA, CBG, CBGA, CBDA, CBDV, CBN, CBL, and combinations thereof.

In a further embodiment, the method wherein the CE comprises CBD at a concentration of between 60% and 99% and at least one other cannabinoid at a concentration of 0.1% to 10% wherein the at least one other cannabinoid is selected from the group consisting of: Δ$^9$-THC, THCA, THCV, Δ$^8$-THC, CBC, CBCA, CBG, CBGA, CBDA, CBDV, CBN, CBL, and combinations thereof; and wherein the CE comprises a total concentration of cannabinoids of between 65% and 99%.

In a further embodiment, the method wherein the composition comprises at least one additional compound selected from the group consisting of: a terpene, a polyphenol, an essential fatty acid, a phytonutrient, and combinations thereof; and wherein the at least one additional compound make up between 0.1% and 50% of the total weight of the composition.

In a further embodiment, the method wherein the composition comprises an oil or a fat as a carrier.

In a further embodiment, the method wherein the effective amount of the composition is an amount sufficient to reach an effective therapeutic level of CBD as measured through systemic plasma levels.

In a further embodiment, the method wherein the composition is administered at an acidic pH. In a further embodiment, the method wherein the acidic pH is between 3.5 and 6.

In a further embodiment, the method wherein the effective amount of the composition is sufficient to reach an effective therapeutic level as measured through systemic plasma levels of CBD.

In a further embodiment, the method wherein the composition further comprises at least one terpene. In a further embodiment, the method wherein the terpene is selected from the group consisting of β-myrcene, β-caryophyllene, linalool, α-pinene, citral, D-limonene, eucalyptol, and combinations thereof.

In a further embodiment, the method wherein the composition further comprises at least one polyphenol. In a further embodiment, the method wherein the polyphenol is selected from the group consisting of: catechins, quercetin, cannflavin A/B/C, rutin, chlorogenic acid, and combinations thereof.

In a further embodiment, the method wherein the composition further comprises an essential fatty acid selected from the group consisting of: an omega 3, an omega 6, an omega 9, and combinations thereof.

In a further embodiment, the method wherein the composition further comprises a phytonutrient. In a further embodiment, the method wherein the phytonutrient is selected from the group consisting of: a tocopherol, a sterol, carotene, an aliphatic alcohol, a mineral, and combinations thereof.

In a further embodiment, the method wherein the CBD is a phytocannabinoid, derived from a *cannabis* extract.

In a preferred embodiment, a method of treating a noncancerous gynecological disorder (NCGD) comprising: (a) taking a gynecological cell from a patient and forming at least one organoid from the gynecological cell; (b) performing a screen on the at least one organoid to determine a *cannabis* extract (CE) responsive to the patient's organoid; and (c) administering the CE to the patient with an effective amount of a composition comprising the CE having between 50% and 99.9% CBD.

In a further embodiment, the method wherein the CE is administered to the patient as an oral form, oromucosal form, nasal form, rectal form, intravaginal form, injectable form, and combinations thereof. In a further embodiment, the method wherein the CE is administered oromucosally and intravaginally.

In a preferred embodiment, a method for treating endometriosis comprising administering to a patient an effective amount of an intravaginal composition comprising a *cannabis* extract (CE) comprising cannabidiol (CBD).

In a further embodiment, the method wherein the endometriosis is an ovarian endometrioma or a deep endometriosis.

A method of treatment of dysmenorrhea or fibroids comprising: administering to a patient an effective amount of an intravaginal composition comprising a *cannabis* extract (CE) comprising cannabidiol (CBD).

In a further embodiment, the method wherein the CE comprises between 50% and 99.9% by weight of CBD.

In a preferred embodiment, use of a therapeutic comprising a *cannabis* extract (CE) for treatment of a gynecological disorder selected from the group consisting of: endometriosis, dysmenorrhea, fibroids, and combinations thereof.

In a preferred embodiment, a therapeutic for treating endometriosis comprising a *cannabis* extract (CE) having an effective amount of CBD.

In a further embodiment, the therapeutic further comprising a carrier.

In a further embodiment, the therapeutic further comprising at least one additional cannabinoid selected from the group consisting of: $\Delta^9$-THC, THCA, THCV, $\Delta^8$-THC, CBC, CBCA, CBG, CBGA, CBDA, CBDV, CBN, CBL, and combinations thereof.

In a further embodiment, the therapeutic further comprising at least one terpene. In a further embodiment, the therapeutic wherein the terpene is selected from the group consisting of: β-myrcene, β-caryophyllene, linalool, α-pinene, citral, D-limonene, eucalyptol, and combinations thereof.

In a further embodiment, the therapeutic further comprising at least one polyphenol. In a further embodiment, the therapeutic wherein the polyphenol is selected from the group consisting of: catechins, quercetin, cannflavin A/B/C, rutin, chlorogenic acid, and combinations thereof.

In a further embodiment, the therapeutic further comprising an essential fatty acid selected from the group consisting of: an omega 3, an omega 6, an omega 9, and combinations thereof.

In a further embodiment, the therapeutic further comprising a phytonutrient. In a further embodiment, the therapeutic wherein the phytonutrient is selected from the group consisting of: a tocopherol, a sterol, carotene, an aliphatic alcohol, a mineral, and combinations thereof.

In a further embodiment, the method or therapeutic further comprising a hormonal therapy, a GnRH therapy, a progestin therapy, an aromatase inhibitor, or combinations thereof.

In a preferred embodiment, a composition for use in a method of treating noncancer gynecological disorders wherein the composition comprises between 1% and 99% by weight of a CE.

In a preferred embodiment, a composition wherein the CE of the composition comprises (a) a FSHE, a BSHE, a CBD isolate, and/or a CBDA isolate; and/or (b) wherein the composition comprises a carrier at between 1% and 99% by weight of the composition; and/or (c) wherein the composition further comprises one or more excipients at between 1% and 50% by weight of the composition.

In a preferred embodiment, a composition for treatment of a noncancer gynecological disorder wherein the composition comprises a *cannabis* extract (CE), wherein the CE comprises between 1% and 100% by weight of the composition and all percentages therein. In preferred embodiments, the CE comprises between 10% and 90% by weight, or 20% by 90% by weight, and preferably between 40% and 80% by weight of the composition. The CE, as detailed herein, is preferably a BSHE, a FSHE, a CBD isolate, or a CBDA isolate. In each of these different CE, the BSHE, the FSHE, the CBD isolate, or the CBDA isolate, they make up between 50% and 99.9% by weight of the CE, with the remaining being waxes, fats, fatty acids and the like. However, preferred embodiments utilize a carrier at between 1% and 99% by weight of the composition, and preferably, one or more additional excipients depending on the use case of the composition. The composition is typically then administered based upon the dosage in mg of CBD being administered. Wherein the amount of the composition required to meet that mg of CBD depends on the quantity of CBD within each of the CE.

In a further preferred embodiment, a method of treatment of a NCGD comprising administering to a patient in need thereof, an effective amount of a composition according to any one of the preceding embodiments. In a preferred embodiment, the method wherein the effective amount is between 20 mg and 4,250 mg of cannabidiol (CBD).

In a preferred embodiment, a composition for use in a method of treating a noncancerous gynecological disorder (NCGD) wherein the composition comprises between 1% and 99% by weight of a *cannabis* extract (CE).

In a further embodiment, the composition wherein the CE of the composition comprises: (a) a full spectrum hemp extract (FSHE), a broad spectrum hemp extract (BSHE), a CBD isolate, a CBDA isolate, or combinations thereof; and/or (b) wherein the composition comprises a carrier at between 1% and 99% by weight of the composition; and/or (c) wherein the composition further comprises one or more excipients at between 1% and 50% by weight of the composition.

In a preferred embodiment, a composition for treatment of a noncancerous gynecological disorder (NCGD) wherein the composition comprises a *cannabis* extract (CE), wherein the CE comprises between 1% and 100% by weight of the composition and all percentages therein.

In a further embodiment, the composition wherein the CE comprises between 10% and 90% by weight, or between 20% and 90% by weight, and preferably between 40% and 80% by weight of the composition.

In a further embodiment, the composition wherein the CE is preferably a full spectrum hemp extract (FSHE), a broad spectrum hemp extract (BSHE), a CBD isolate, or a CBDA isolate. In a further embodiment, the composition wherein the BSHE and/or the FSHE and/or the CBD isolate and/or the CBDA isolate constitute between 50% and 99.9% by weight of the CE.

In a further embodiment, the composition comprising a carrier at between 1% and 99% by weight of the composition.

In a further embodiment, the composition further comprising at least one or more additional excipients.

In a further embodiment, the composition wherein the composition is a mucosal composition.

In a further embodiment, the composition comprising between 20 mg and 4,250 mg of CBD.

In a preferred embodiment, a method of treating a noncancerous gynecological disorder (NCGD) comprising administering to a patient an effective amount of a composition. In a further embodiment, the method wherein the effective amount is between 20 mg and 4,250 mg of cannabidiol (CBD).

BRIEF DESCRIPTION OF THE FIGURES

FIGS. 1A, 1B, 1C, 1D, 1E, 1F, and 1G depict endometrial cancer cells being treated with a *cannabis* extract comprising CBD, with FIG. 1A showing a diagram of the process of capturing the data regarding protein expression, FIG. 1B depicting protein differentiation numbers; FIG. 1C depicting upregulated and down regulated cells in the vehicle and with a *cannabis* extract comprising CBD treatment; FIG. 1D depicting the top 20 up and down regulated proteins in ECC treated cells; and FIG. 1E depicting the *cannabis* extract's effects on signaling and trafficking of various physiological and pathophysiological pathways. FIG. 1F depicts cannabinoid receptor 1 protein expression in an endometrial cancer cell; and FIG. 1G depicts cannabinoid receptor 2 protein expression in an endometrial cancer cell.

FIGS. 6A and 6B depict further graphs of BSHE, FSHE, and CBD isolate for 1, 2, 3, 4, 5, 7, and 10 µg/mL concentration on endometrial organoids, and FIG. 6B depicts a graphical depiction of response to CBDA for endometrial organoids.

FIG. 7 depicts a graphical chart of endometrial cancer tumor volumes within mice, wherein the mice were injected with patient derived endometrial cancer cells. The data shows the change in tumor volume from day 7 to day 21 and depicting the therapeutic efficacy of the various *cannabis* extracts on the tumor volumes.

DETAILED DESCRIPTION OF THE INVENTION

Figures 1D, 1E:
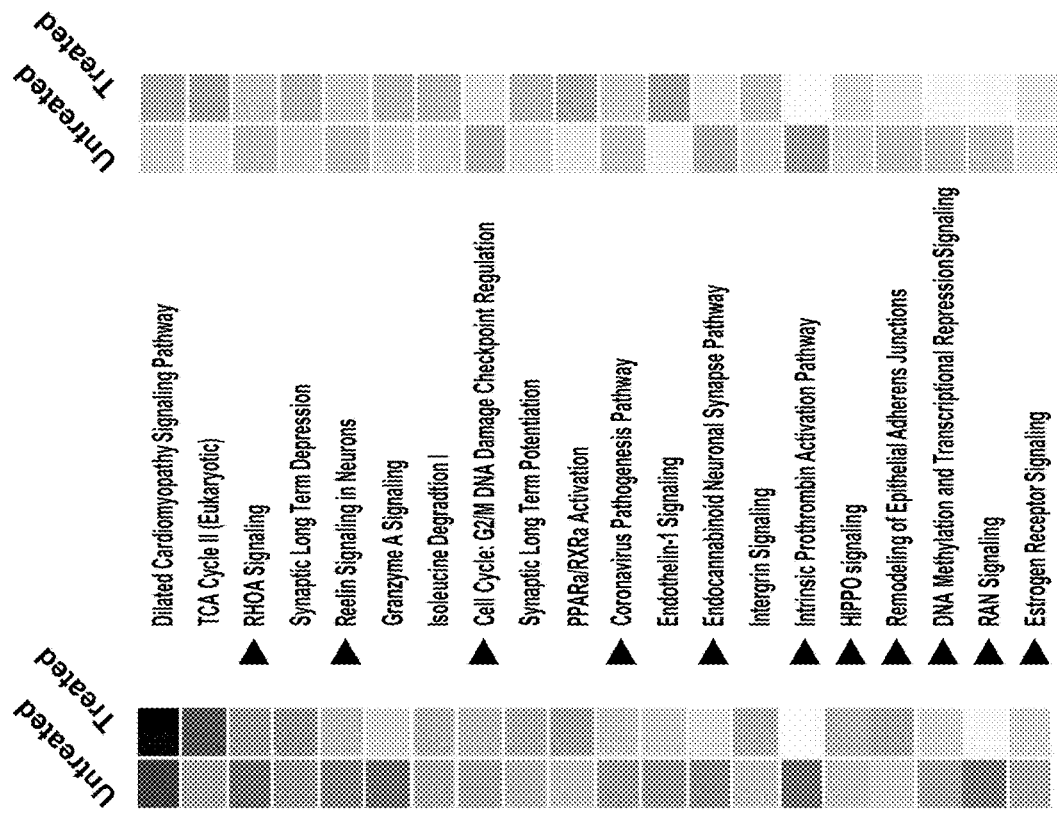

Various embodiments are described more fully hereinafter with reference to the accompanying drawings, which form a part hereof. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be therapeutic products, methods of treatment, use of therapeutics in treating the one or more afflictions of noncancerous gynecological disorders. The following detailed description is, therefore, not to be taken in a limiting sense.

As used herein, the term "about" means plus or minus 5% of the numerical value of the number with which it is being used. Therefore, about 50% means in the range of 45%-55%, about 20 mg means the range including 19 mg to 21 mg, and the like.

"Administering" when used in conjunction with a therapeutic means to administer a therapeutic directly to a subject, whereby the agent positively impacts the target. "Administering" the therapeutic drug or compound may be accomplished by, for example, injection, oral administration, topical administration, mucosal administration and/or in combination with other known techniques. The administering techniques may further include heating, radiation, chemotherapy, ultrasound, and the use of delivery agents. Preferably in the present disclosure the administration is through oral, oral mucosal/sublingual, and/or intravaginal dosage forms. Such intravaginal forms are intended to be inserted into the vagina, typically with a carrier, wherein the active ingredients pass through the vaginal mucosal membrane. The active ingredients may also be provided in an oral form, to be swallowed. Another oral form is an oral mucosal application, which is often provided as a sublingual application, which, while it is ultimately swallowed to enter the stomach, is intended to be held in the mouth, for example under the tongue, and the active ingredients pass through the oral mucosal membrane before being swallowed or passed into the stomach by salivary action or active swallowing of the materials or both.

As used herein, "broad spectrum hemp extract" (BSHE) is a composition derived from the *Cannabis* genus of plants which has undergone at least some purification in order to refine the extract. Typically, a BSHE comprises between 60 and 99.9% CBD and least one additional cannabinoid, selected from the group consisting of $\Delta^9$-THC, THCA, THCV, $\Delta^8$-THC, CBC, CBCA, CBG, CBGA, CBDA, CBDV, CBN, CBL, and combinations thereof at between 0.1 and 40%.

As used herein "*cannabis* extract" (CE) and "*cannabis* extract comprising CBD" mean a composition derived from the *Cannabis* genus of plants (including hemp). Typically, a *cannabis* extract contains cannabidiol (CBD), and more typically comprises both CBD and at least one additional cannabinoid selected from the group consisting of $\Delta^9$-THC, THCV, $\Delta^8$-THC, CBC, CBCA, CBG, CBGA, CBDA, CBDV, CBN, CBL, and combinations thereof at between 0.1 and 40%. *Cannabis* extracts according to the present invention are typically enriched in cannabidiol, and may comprise between 1 and 99.9% CBD, preferably between 20 and 99.9% CBD, more preferably between 50 and 99.9% CBD, even more preferably between 70 and 99.9% CBD, and most preferably between 90 and 99.9% CBD. When described herein, the percent of the *cannabis* extract, means that, as in the preceding sentence the total cannabinoids make up between 50 and 99.9% by weight, or 70-99% by weight or 90 to 99% by weight of the *cannabis* extract. Full spectrum hemp extract, broad spectrum hemp extract, CBD isolate, and CBDA isolate are forms of *cannabis* extract utilized herein, as non-limiting examples of the CE. Throughout the application, the term CBD is often used interchangeably with CE, to mean the CE product containing the particular amount of CBD. while in other instances, which are obvious to the reader, the CBD refers to a CBD isolate, which means the CE was processed to remove and isolate CBD, removing virtually all other components of the CE.

As used herein, "coadministering" means administering a *cannabis* extract and the a second therapeutic agent no more than 72 hours apart, preferably no more than 48 hours apart, and more preferably no more than 24 hours apart, for example no more than 12 hours apart, no more than 6 hours apart, no more than 4 hours apart, no more than 3 hours apart, no more than 2 hours apart, no more than one hour apart, no more than 30 minutes apart, or simultaneously.

As used herein, "concomitantly" means a first formulation and a second formulation administered to a patient no more than 72 hours apart, preferably no more than 48 hours apart, and more preferably no more than 24 hours apart, for example no more than 12 hours apart, no more than 6 hours apart, no more than 4 hours apart, no more than 3 hours apart, no more than 2 hours apart, no more than one hour apart, no more than 30 minutes apart, or simultaneously.

As used herein, "full spectrum hemp extract" (FSHE) is a composition derived from the *Cannabis* genus of plants which contains CBD, and quantities of THC above 0, preferably, between 0.01 and 5%, and most preferably between 0.01% and 0.3%. The FSHE may comprise additional cannabinoids, yielding a product that comprises at least 50-99% CBD, at least 0.01% to 10% of all THC ($\Delta^9$-THC, THCA, THCV, $\Delta^8$-THC), and total cannabinoids of between 50% and 99% of the weight of the CE.

For the purposes of the present application, "hemp" is a *cannabis* plant having a $\Delta^9$-THC content of 0.3% or less by dried weight.

By "pharmaceutically acceptable," it is meant that the components including, but not limited to the carrier, diluent, adjuvant, or excipient must be compatible with the other ingredients of the formulation and not deleterious to the recipient thereof.

As used here, the term "composition" is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s) and the inert ingredient(s) that make up the carrier, as well as any product which results, directly or indirectly, from combination, complexation, or aggregation of any two or more of the ingredients or from dissociation of one or more of the ingredients, or from other types of reactions or interactions of one or more of the ingredients. Accordingly, the pharmaceutical compositions of the present invention encompass any composition made by admixing a compound or compounds of the present invention and a pharmaceutically acceptable carrier.

As used herein, the terms "agent," "active agent," "therapeutic agent," or "therapeutic" mean a compound or composition utilized to treat, combat, ameliorate, prevent, or improve an unwanted condition or disease of a patient. Furthermore, the terms "agent," "active agent," "therapeutic agent," or "therapeutic" encompass a *cannabis* extract and/or additional agents as described in the present disclosure.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue to achieve the therapeutic response. Specifically, the therapeutic shall be effective in treating noncancerous gynecological disorders.

The terms "treat," "treated," or "treating" as used herein refer to both therapeutic treatment and prophylactic or preventative measures wherein the object is to prevent or slow down (lessen) an undesired physiological condition, disorder, or disease, or to obtain beneficial or desired clinical results. For the purposes of this disclosure, beneficial or desired results include, but are not limited to, alleviation of symptoms; diminishment of the extent of the condition, disorder, or disease such as a reduction in the size of a tumor; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease.

An association between endometriosis and Endometrial cancer (EC) has been indirectly suggested by epidemiological, biological, and molecular studies, and recent research suggests a genetic basis for overlap. Studies have shown endometriosis heritability of approximately 50% and EC heritability of 27%. A review of published SNP's evidence identifies a genetic overlap between endometriosis and endometrial cancer in the genetic correlation analysis, with more SNPs than could expected by chance associated in the same direction of effect. In the cross-disease metanalysis, after adjustment, 13 SNPs that appeared to be involved in replication. SNP rs2475335, which is located on chromosome 9p23, was most significantly associated with both diseases (P=4.9×10$^{-8}$). This SNP is housed within the protein tyrosine phosphatase receptor type D (PTPRD) gene. PTPRD deletions and mutations have been found in endometrial tumors. In addition, PTPRD exerts an effect on the STAT3 pathway, which has been identified as relevant to both endometriosis and endometrial cancer. Furthermore, endometriosis and EC are associated with higher levels of estrogen exposure, with a lessened risk related to use of oral contraceptives and progesterone-containing hormonal therapies.

Endometriosis is a painful disorder in which tissues similar to those of the uterine lining grows outside of the uterus. Endometriosis affects 6-10% of reproductive aged women and 35-50% of infertile women. Endometriosis and endometrial cancer are associated with higher levels of estrogen exposure, with a lessened risk related to use of oral contraceptives and progesterone-containing hormonal therapies. Endometriosis most commonly involves ovaries, fallopian tubes, and the tissues lining the pelvis, including the vagina. With endometriosis, the endometrial tissues act as normal uterine cells, in that they thicken and break down, and thus bleed at each menstrual cycle. However, in many cases, where the tissue has no way to exit the body, it becomes trapped. When endometriosis involves the ovaries, cysts called endometriomas may form. A key concern is the formation of irritation and development of scar tissue and adhesions, which are bands of fibrous tissue that can cause pelvic tissues and organs to stick together. This results in a highly common side effect, which is pain, sometimes severe, especially during menstrual periods. Further, in some cases, the impacts cause fertility issues.

The causes of endometriosis are not certain, however some possible explanations include: retrograde menstruation, where endometrial cells flow back through the fallopian tubes, instead of out of the body; the transformation of peritoneal cells, in what is known as induction theory, wherein hormones or immune factors promote transformation of peritoneal cells; embryonic cell transformation, where hormones transform certain embryonic cells into endometrial like cells during puberty; surgical scar implantation, which occurs after a surgical procedure; endometrial cell transport through the blood vessels of lymphatic system; or from an immune system disorder.

Treatment for endometriosis is limited, with the most common treatments including pain medication, hormone therapy, and surgical procedures. Hormone therapy treatment include various forms of hormonal contraceptives, gonadotropin-releasing hormone (Gn-RH) agonists and antagonists, progestin therapy, and aromatase inhibitors. Hormonal therapy for contraceptives seeks to shorten menstrual flow and have lighter periods, which reduces some of the side effects of endometriosis. Gn-RH therapy seeks to lower estrogen levels and cause endometrial cells to shrink, essentially causing an artificial menopause. Progestin therapy seeks to halt menstrual periods and can be achieved through intrauterine devices, contraceptive implants or injections. Finally, aromatase inhibitors reduce estrogen in the body, similar to some of the above treatments. These may be used alone or in combination with one another or with additional therapeutic treatments.

Surgical options include removal of endometriosis implants as the most conservative option while more aggressive surgical procedures include the removal of the uterus and/or ovaries. Accordingly, the treatment options remain limited. Furthermore, even with the most aggressive surgical options, endometrial tissues often remain and continue to cause pain and discomfort. Based on the parallels to EC, the incidence rates of EC and endometriosis are relevant to the therapeutic needs for treatment.

EC is one of the most frequently diagnosed gynecological cancers worldwide, and its prevalence has increased by more than 50% over the last two decades. Endometrial cancer (also called endometrial carcinoma) starts in the cells of the inner lining of the uterus (the endometrium). This is the most common type of cancer in the uterus. Endometrial carcinomas can be divided into different types based on how the cells look under the microscope. (These are called histologic types.) They include: Adenocarcinoma (most endometrial cancers are a type of adenocarcinoma called endometrioid cancer [see below]); Uterine carcinosarcoma or CS; Squamous cell carcinoma; Small cell carcinoma; Transitional carcinoma; and Serous carcinoma. Clear-cell carcinoma, mucinous adenocarcinoma, undifferentiated carcinoma, dedifferentiated carcinoma, and serous adenocarcinoma are less common types of endometrial adenocarcinomas. They tend to grow and spread faster than most types of endometrial cancer. They often have spread outside the uterus by the time they're diagnosed.

Most endometrial cancers are adenocarcinomas, and endometrioid cancer is the most common type of adenocarcinoma, by far. Endometrioid cancers start in gland cells and look a lot like the normal uterine lining (endometrium). Some of these cancers have squamous cells (squamous cells are flat, thin cells), as well as glandular cells. There are many variants (or sub-types) of endometrioid cancers including: Adenocarcinoma, (with squamous differentiation); Adenoacanthoma; Adenosquamous (or mixed cell); Secretory carcinoma; Ciliated carcinoma; Villoglandular adenocarcinoma.

The grade of an endometrial cancer is based on how much the cancer cells are organized into glands that look like the glands found in a normal, healthy endometrium. In lower-grade cancers (grades 1 and 2), more of the cancer cells form glands. In higher-grade cancers (grade 3), more of the cancer cells are disorganized and do not form glands. Grade 1 tumors have 95% or more of the cancer tissue forming glands. Grade 2 tumors have between 50% and 94% of the cancer tissue forming glands. Grade 3 tumors have less than half of the cancer tissue forming glands. Grade 3 cancers tend to be aggressive (they grow and spread fast) and have a worse outlook than lower-grade cancers.

Grades 1 and 2 endometrioid cancers are type 1 endometrial cancers. Type 1 cancers are usually not very aggressive and they don't spread to other tissues quickly. Type 1 endometrial cancers are thought to be caused by too much estrogen. They sometimes develop from atypical hyperplasia, an abnormal overgrowth of cells in the endometrium. A small number of endometrial cancers are type 2 endometrial cancer. Type 2 cancers are more likely to grow and spread outside the uterus, they have a poorer outlook (than type 1 cancers). Doctors tend to treat these cancers more aggressively. They don't seem to be caused by too much estrogen. Type 2 cancers include all endometrial carcinomas that aren't type 1, such as papillary serous carcinoma, clear-cell carcinoma, undifferentiated carcinoma, and grade 3 endometrioid carcinoma. These cancers don't look at all like normal endometrium and so are called poorly differentiated or high-grade. Uterine carcinosarcoma (CS) starts in the endometrium and has features of both endometrial carcinoma and sarcoma. (The sarcoma is cancer that starts in muscle cells of the uterus.) In the past, CS was considered a different type of uterine cancer called uterine sarcoma (see below), but doctors now believe that CS is an endometrial carcinoma that's so abnormal it no longer looks much like the cells it came from (it's poorly differentiated). Uterine CS is a type 2 endometrial carcinoma. CS tumors are also known as malignant mixed mesodermal tumors or malignant mixed mullerian tumors (MMMTs). They make up about 3% of uterine cancers.

Despite the understanding of the major signaling pathways driving the growth and metastasis of endometrial cancer, clinical trials targeting these signals have reported poor outcomes. The heterogeneous nature of endometrial cancer is suspected to be one of the key reasons for the failure of targeted therapies. EC is typically understood to be split into four molecular subtypes, including hypermutated cases with POLE mutations and 25-30% harboring a microsatellite instability (MSI) phenotype with mismatch repair deficiency (dMMR). Some of these subtypes are thus treated with PD-1/PD-L1 inhibitors, or with immune checkpoint inhibitors, and other molecules such as pembrolizumab or Lenvatinib. However, these molecules, like first line chemotherapy agents, have high toxicity profiles and thus have significant co-morbidities associated with their use. Furthermore, being targeted, they sometimes miss the heterogeneous nature of the cancer.

In some cases, EC poses few, if any symptoms, and is one of the key reasons why many EC patients only discover the disease at later stages. However, for others some of the symptoms of EC are masked by normal reproductive cycle symptoms, by noncancerous endometriosis, as well as those occurring during menopause. Accordingly, some women miss early signs of EC due to confounding factors. However, for others, EC presents with abnormal uterine bleeding that allows for a portion of patients to detect disease at an early stage. Once detected, treatment for EC is almost always surgical removal of the tissue and organ, combined with chemotherapy, and/or radiation therapy. In some cases, early detection of EC may prevent the need for chemotherapy or radiation therapy, as the cancer is contained only in the uterus. However, EC is quite nefarious, and even a few missed cells, which have migrated from the uterus, then allow for proliferation of the diseased tissues, thus providing evidence for the need for chemotherapy even at early stage diagnosis after removal of the organs.

For both early stage (Stage I and II EC), and for Stages III and IV EC, first line treatment for EC almost always includes hysterectomy and bilaterial salpingo-oophorectomy. In most cases, this is followed by chemotherapy. In view of the significant side effects of chemotherapy, a small portion of stage I and II patients may omit or reduce chemotherapy use as compared to Stages III and IV patients. Chemotherapy is virtually always given to stage III or stage IV EC patients, and often with several rounds of therapy, with the goal of optimizing the risks and the rewards. For Stage III and IV EC, accordingly, organ and tumor removal is typically followed by chemotherapy treatment to capture metastatic disease, as the endometrial cancer cells have often already migrated from the uterus. However, it is well-known that chemotherapy agents are somewhat indiscriminate in their killing, and thus significant secondary impacts occur to the patient leading to impacts on the quality of life. Indeed, even where the chemotherapy is effective in treating the cancer, the toxic effects of the chemotherapy often prove fatal overtime. In virtually all cases, chemotherapy is given in a cycle, meaning a drug or combination of drugs are given for a period of usually 2-6 weeks, and then a rest period, followed by a second or more treatment period. Drugs that are currently utilized for endometrial cancer treatment including paclitaxel, carboplatin, doxorubicin, cisplatin, docetaxel, and the combined therapy of carboplatin or cisplatin with paclitaxel, and others.

Thankfully, endometriosis, while related to endometrial cancer, dose not metastasize throughout the body, and does not undergo the unregulated growth hallmark of cancer. Accordingly, chemotherapeutic agents are not indicated for endometriosis and other noncancerous disorders of the female reproductive system.

Given the widespread presence of the ECS in the mammalian body, and particularly in the reproductive system, the effects of a *cannabis* extract (CE) including CBD on endometrial cancer cell protein expression was examined. Proteomics is the large-scale study of proteins, where a proteome is the entire set of proteins produced by the sample under investigation. Proteomes will differ from cell to cell and from time to time. Thus, the comparison of protein expression in untreated cells as compared to treated cells provides insight as to which proteins change expression in the endometrial cancer cells and which proteins remain the same. With this knowledge, additional, targeted research may ensue. Referring to FIG. 1A, endometrial cancer cells (ECC) were either treated with a CE with CBD (1 μg/mL) or left untreated as a control (vehicle). After treatment, proteins were extracted from the test cells and the control cells and digested for analysis by liquid chromatography (LC) tandem mass spectrometry (MS/MS). Referring to FIG. 1B, the Venn diagram shows the results of LC-MS/MS analysis which is that treated cells expressed 2,842 different proteins than untreated cells, untreated cells expressed 2,681 different proteins than treated cells, and treated and untreated both expressed 3,747 common proteins. Clearly, based on protein expression differences, treatment with as little as 1 μg/mL CE with CBD had a clear impact on proteins that were exclusively expressed and proteins that were no longer expressed. FIG. 1C compares the degree to which certain proteins were expressed (or not expressed) in untreated cells and treated cells.

Figure 1G:
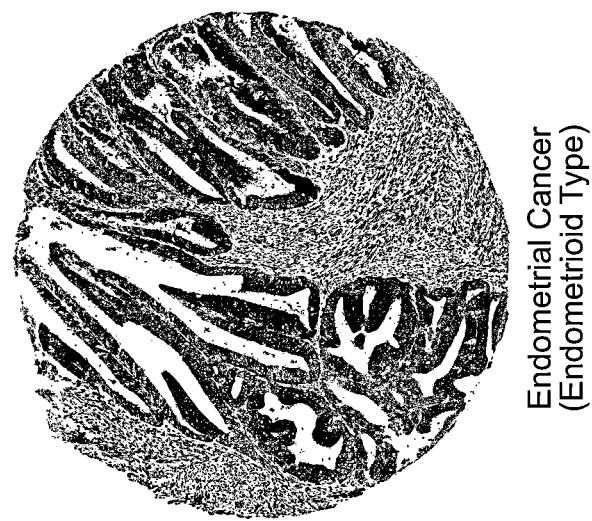

Referring to FIG. 1D, of the thousands of proteins that were differentially expressed with treated and untreated cells, the top 20 upregulated (e.g., in treated cells only) and downregulated (e.g., in untreated cells only), are identified and enumerated. Now referring to FIG. 1E, the effect of treatment with CE with CBD on signaling and trafficking of various physiological and pathophysiological pathways is shown. As one example, proteins associated with Endocannabinoid Neuronal Synapse are shown to be upregulated in untreated cells and downregulated in treated cells. Lastly, referring to FIG. 1F, a tissue sample taken from a patient with endometrial cancer was selectively stained to show CB1 receptor expression. FIG. 1G is a similar tissue sample selectively stained to show CB2 receptor expression.

At about the same time as the above experiments were taking place, the response of organoids derived from endometrial cancers to CE with CBD were also studied. Generally, patients with EC were identified and tumor cells were collected. The EC tumor cells were used to generate patient derived organoids, the method of which is described below in the Methods section. As the name suggests, organoids are miniature structures that emulate organs in all their complexity. They are derived from stem cells collected via biopsies and/or resected healthy tissues or tumors. In culture, they self-organized into three-dimensional tissues that mimic the tissues of the individual patient from which they were derived. That is, organoids have the same genetic instructions as the individual from which they were derived and thus demonstrate identical mutations, proliferation, and disease progression as their human counterpart. Organoids can be made to replicate organs with differentiated cell types or to express selected aspects of identified cells of interest. Unlike traditional cell line models associated with high failure rates in clinical trials, organoids' responses precisely and directly translate to human responses. Organoids are well established and have already transformed medical research in providing breakthroughs in treating cystic fibrosis, pancreatic cancer, diabetes, and other diseases. In a simplified example, imagine organoids as clones of an individual's organ. In essence, it is a living, growing avatar of a distinct patient existing outside the body. The avatar will mimic tumor growth and respond to treatment cancer just as it would inside the body. This personalized replica identifies allows for identification of individualized, targeted treatment in a matter of days. It allows a patient to avoid wasting time and risking toxicity with ineffective therapies.

Figure 2A:
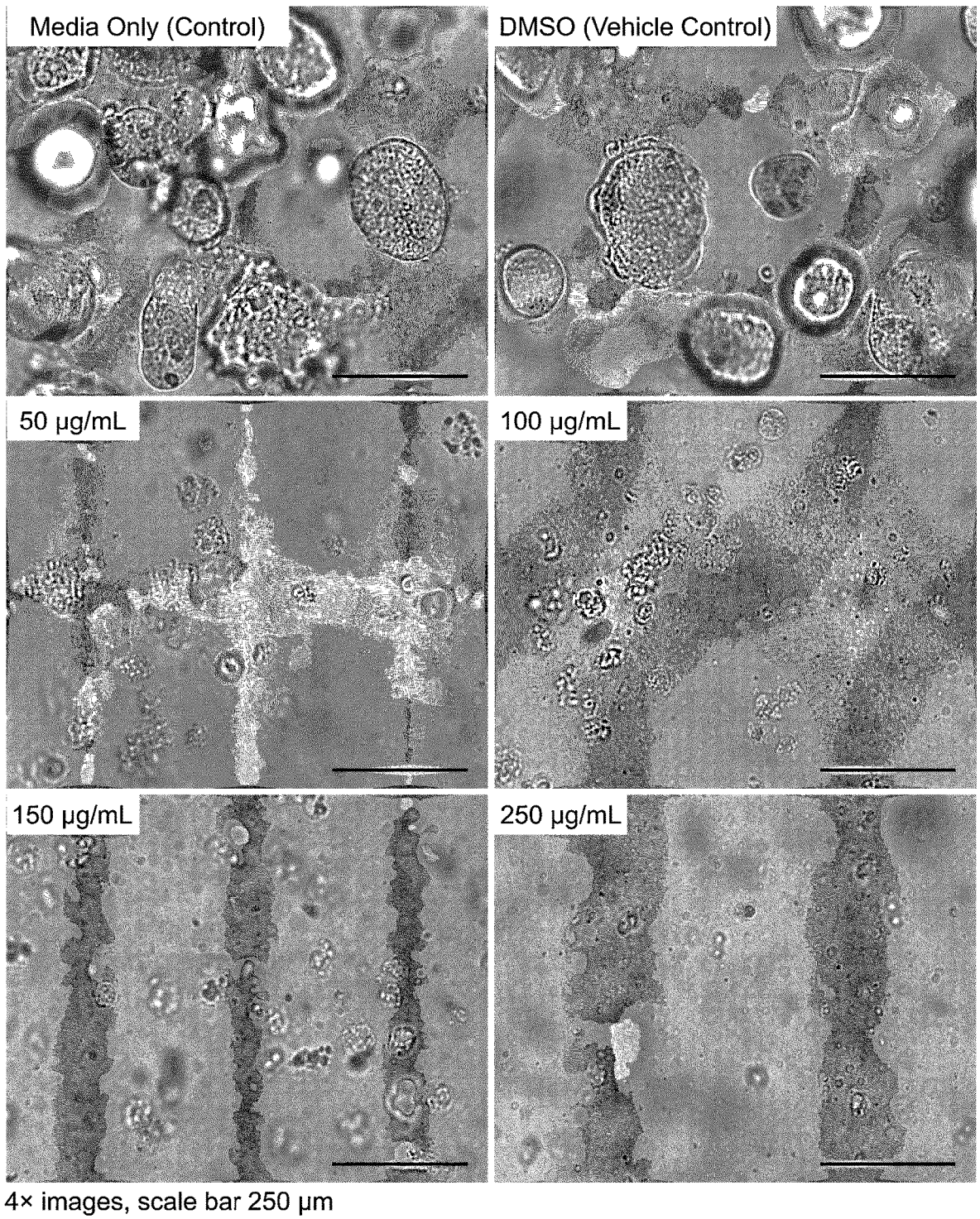
FIGS. 2A and 2B depict endometriosis based organoids treated with a *cannabis* extract, with FIG. 2A depicting cells with *cannabis* extracts comprising varying amounts of CBD as delivered through BSHE. Notably, FIG. 2B summarizes the results showing a minimum inhibitory concentration (the absence of organoids), but as low as 50 µg, and all values above.
Figure 2B:
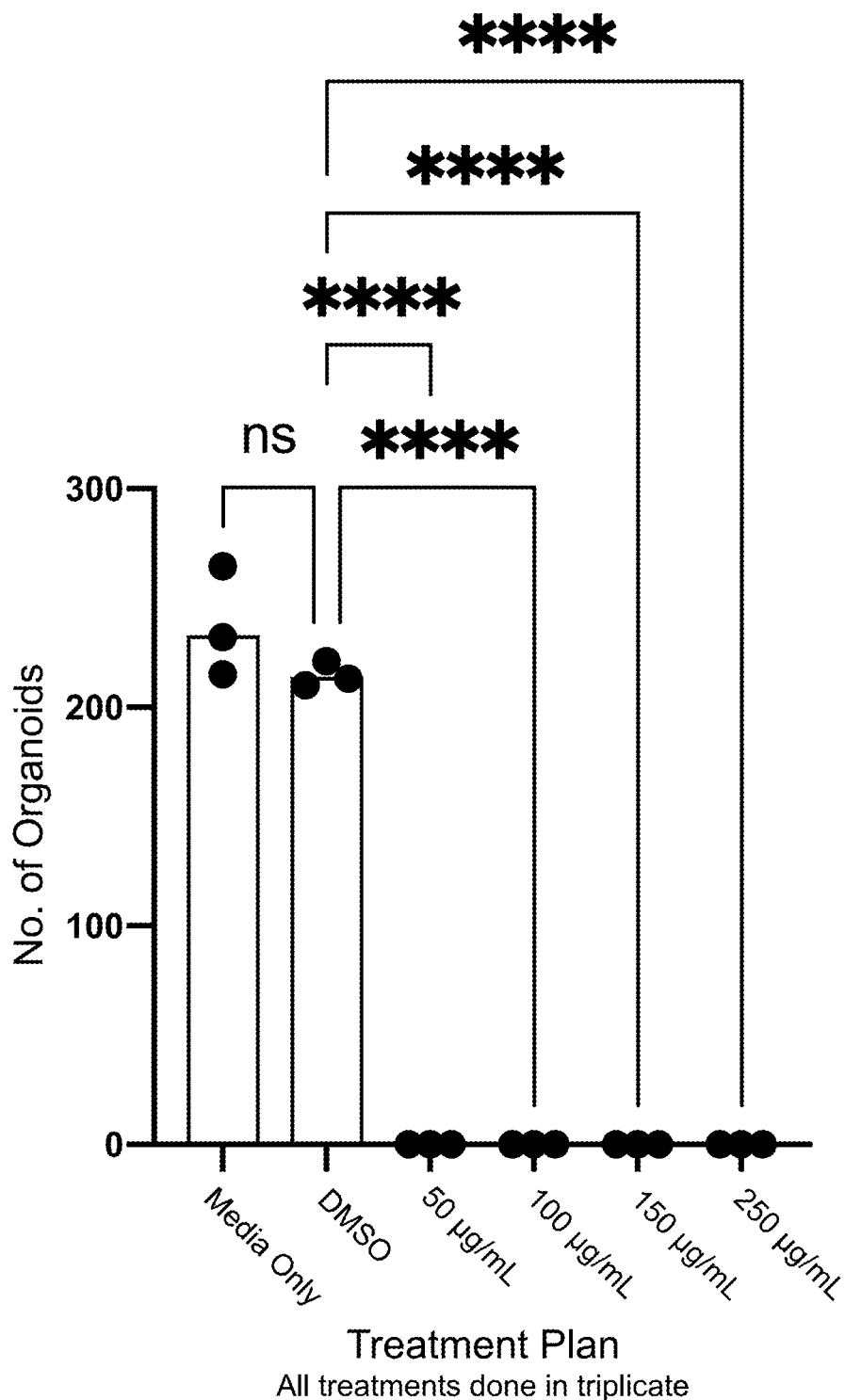

Initial experiments on endometriosis based organoids derived from endometrial cells used 250 µg/mL of a BSHE comprising CBD as the lowest dose for treatment. This dosage was 100% effective in killing the endometriosis organoids, which was certainly unexpected. Subsequent experiments used 150 µg/mL of the BSHE as the lowest dose for treatment. Again, 100 µg/mL was 100% effective in killing the endometrial cancer organoids. Thereafter, endometriosis organoids were treated with lower doses of the BSHE, with 50 µg/mL as the lowest dose tested. As can be seen in FIG. 2A, the organoids created from endometrial cells were treated with media only, which is the growth media in which the organoids were grown, the vehicle, which is the just the solvent used to deliver the BSHE to the other organoids, and then test dosages of 50 µg/mL, 100 µg/mL, 150 µg/mL, and 250 µg/mL each concentration being delivered the vehicle. As can be in FIG. 2B (and 2A) the vehicle and the media only show nearly the same number of organoids. But at a concentration as low as 50 µg/mL BSHE was able to completely kill the EC organoids. The higher doses of BSHE at 100 µg/mL and 150 µg/mL also showed a 100% kill rate of the EC organoids. Each of the tests of FIG. 2 were run at least in triplicate, including the vehicle alone, which was dimethyl sulfoxide (DMSO).

For comparison, the doses in which the organoids were treated convert to human equivalent doses of 500 and 1000 mg a day respectively for the lowest doses. Currently prescribed dosages of CBD isolate (in the United States) are between 5 and 50 mg of CBD/kg. An average weight of between 65 and 85 kg (about 143 pounds to about 187 pounds) yields doses of between 325 to 4250 mg a day of CBD. Our actual tests, therefore, range perfectly within these guidelines. We believe that the higher end of the human dosing range is fully appropriate in this case (endometriosis) as well, which would replicate the experiments performed at 100 µg/mL and higher. Especially as the alternative to such CBD dose is NSAID or other pain medication, surgical removal, or other hormonal therapy, none of which have shown long term successes. Finally, some new alleged treatments have low success rates and significant side effects limiting their use.

Soon after the experiments detailed above a 31-year-old Caucasian female came to us. She was initially diagnosed with endometriosis, and later diagnosed with endometrial cancer after presenting with significant pain and discomfort. She had already undergone a total hysterectomy and bilateral salpingo-oophorectomy followed by five rounds of chemotherapy. Each of the first five rounds of chemotherapy was a combined chemotherapy with Paclitaxil/Carboplatin. The treatments were ultimately ineffective, and she did not proceed with a sixth round of chemotherapy with these agents due to the ineffectiveness of the prior rounds. Thereafter she was treated with Abemaciclib followed by Atezolizumab, which also failed and resulted in severe adverse effects. As a result of her lack of response to chemotherapy, she was deemed to have chemoresistant endometrial cancer.

When she came to us her endometrial cancer was stage IV and due to the chemoresistance and aggressive nature of the cancer she also had extensive metastatic disease throughout her body. Affected areas included her brain, breasts, heart, stomach, lungs, peritoneum, and lymphatic system. PET scans and other techniques were used to determine the size of metastatic nodes, which ranged from 11×7 mm to 29×10 mm. See, Tables 1 and 2, below. In view of the experiments detailed above, organoids were crafted from the patient's endometrial cancer to assess her response to alternative chemotherapies (after failing seven chemotherapy rounds) in view of her chemoresistance and to the BSHE that was being tested. Her organoids demonstrated a partial response to gemcitabine/capecitabine (GemCap), a combination chemotherapy she had not yet been offered, and a significant response to the BSHE. As such, she began standard protocol GemCap treatment in combination with a regime of 30 mg of BSHE twice daily via oral mucosal delivery and 75 mg of FSHE once daily via intravaginal delivery. Thus, her total daily dose of *cannabis* extract including CBD was 135 mg. After 12 weeks of treatment, a follow up PET scan reported astounding results, which are detailed in Tables 1 and 2.

TABLE 1

A COMPARISON OF THE METABOLIC RESPONSE IN THE PATIENT'S LYMPH NODES BEFORE AND AFTER TREATMENT

| | Before Treatment | | After Treatment | |
| --- | --- | --- | --- | --- |
| Area | Size | SUV max | Size | SUV |
| Left Supra-clavicular: | 25 × 16 mm | 18.1 | 7 × 4 mm | No longer measurable on PET |
| Subcarinal | 21 × 14 mm | 16.1 | 9 × 5 mm | No longer measurable on PET |
| Left Hilar | 18 × 10 mm | 10.5 | 8 × 5 mm | No longer measurable on PET |

TABLE 1-continued

A COMPARISON OF THE METABOLIC RESPONSE IN THE PATIENT'S LYMPH NODES BEFORE AND AFTER TREATMENT

| Area | Before Treatment | | After Treatment | |
|---|---|---|---|---|
| | Size | SUV max | Size | SUV |
| Left External Iliac | 15 × 12 | 17.8 | 8 × 5 mm | No longer measurable on PET |
| Aortico-pulmonary | 29 × 10 | 15.1 | | No longer measurable on CT or FDG PET |
| Left internal Mammary | 10 × 8 mm | 9.2 | | No longer measurable on CT or FDG PET |
| Right internal mammary | 11 × 7 mm | 3.9 | 5 × 3 | No longer measurable on PET |
| Left Gastric | 23 × 15 mm | 13.2 | 12 × 7 mm | No longer measurable on PET |
| Left of SMA | 20 × 19 mm | 10.4 | 7 × 4 mm | No longer measurable on PET |

TABLE 2

COMPARISON OF THE METABOLIC RESPONSE IN THE PATIENT'S PULMONARY METASTASES AND PERITONEUM BEFORE AND AFTER TREATMENT.

| Area | Before Treatment | | After Treatment | |
|---|---|---|---|---|
| | Size | SUV max | Size | SUV |
| Left Lower lobe Lateral | 18 × 13 mm | 17.9 | 6 × 3 mm | no longer measurable on PET |
| Right Upper lobe Central | 19 × 14 mm | 17.9 | | no longer measurable on CT or FDG PET |
| Peritoneal | 22 × 10 mm | 7.2 | | No longer measurable on PET |

Amazingly, radiology concluded a complete metabolic response to treatment. Notably, significant reductions in the size of metastases were documented. Furthermore, there were no new enlarged or hyper metabolic nodes within the neck, chest, abdomen, pelvis, or inguinal regions to suggest new sites of metastatic adenopathy. And there were no new hypermetabolic pulmonary metastases, no lymphangitis, no pleural or pericardial effusion, no abnormal metabolism in the solid abdominal organs, and no evidence of solid abdominal visceral or metastatic disease on diagnostic CT. Previously demonstrated malignancy ascites in the pelvic region were near completely resolved and there was complete metabolic response in peritoneal deposits. For example, the peritoneum had one of the largest deposits before treatment of 22×10 mm with a SUV max of 7.2 and after treatment was no longer measurable via PET, with no new hypermetabolic peritoneal deposits. Additionally, there were no abnormal metabolism in the brain, no suspicious lesions on the low dose, non-contrast CT, and no abnormal metabolism in bone to suggest osseous metastasis. Furthermore, her endometriosis was also resolved and in control at the time of her subsequent CT scans.

Additional results from testing agents on organoids derived from the patent described above are shown in Table 3. The IC50 values were calculated from such tests. This value indicates the dosage at which 50% of the organoids were killed due to treatment. The C. values As can be seen in the table, only a few IC50 values were able to be calculated as the remaining agents did not have enough of an inhibitory effect to be able to determine an IC50 value. In other words, they were not effective at killing the patient's organoids.

TABLE 3

EFFECTS OF VARIOUS AGENTS ON PATIENT DERIVED ORGANOIDS.

| Drug | $C_{max}^2$ | Calculated $IC_{50}$ PD3D Cell Culture |
|---|---|---|
| Cisplatin | 3.62 µM | 5.05 µM |
| Samotolisib | 0.6 µM | 0.87 µM |
| Panobinostat | 0.06 µM | 0.11 µM |
| Niclosamide | 0.31 µM | 0.6 µM |
| Etoposide | 33.8939875 | 87.30551 |
| Temozolomide | 37.6 µM | 105.7 µM |
| Artesunate | 8.58 µM | 38.4 µM |
| Metformin | 10.84 µM | Not Reached |
| Colchicine | 0.006 µM | Not Reached |
| Glutathione | 150 µM | Not Reached |
| Ascorbic Acid | 436.2 µM | Not Reached |
| Hydroxychloroquine | 0.12 µM | Not Reached |
| Pomalidomide | 0.27 µM | Not Reached |
| Sunitnib | 0.09 µM | Not Reached |
| Dichloracetate | 330 µM | Not Reached |
| Bevacizumab | 0.92 µM | Not Reached |
| Kadcyla | 0.53 µM | Not Reached |
| Cetuximab | 1.4 µM | Not Reached |
| Crizotinib | 0.23 µM | Not Reached |
| Propranolol | 0.102 | Not Reached |
| Ruxolitinib | 0.587 | Not Reached |
| Capecitabine (5-FU) | 2.22174388 | Not Reached |
| Cobimetinib | 0.51383399 | Not Reached |
| Ponatinib | 0.13707376 | Not Reached |
| Pemetrexed | 290.623674 | Not Reached |
| Lenvatinib | 0.99987584 | Not Reached |
| Olaparib | 17.4680519 | Not Reached |

A few of the tested agents were slightly effective on organoid samples, but the IC50 number remained below the Cmax, identifying them as poor choices for therapeutic use. Notably, none of the agents listed in Table 3 were as effective as the *cannabis* extract used to treat the patient.

In addition to the agents listed above, several other drugs were tested to see if they influenced organoid growth. The results of which are shown in Table 4. In this case, results are shown as the % of cells that died compared to control Notably, paclitaxel was shown to be wholly ineffective, and thus the 39% cell death is indicative of the need to greatly increase the dosage for successful treatment. This is consistent with the patient's actual lack of response to treatment with paclitaxel.

TABLE 4

EFFECTS OF VARIOUS AGENTS ON THE DEATH OF PATIENT DERIVED ORGANOIDS.

| Drug Name | % Cell Death |
|---|---|
| 5-Fluorouaracil/Capecitabine | 61 |
| Gemcitabine | 56 |
| Bleomycin | 53 |
| Irinotecan | 51 |
| Mitoxantrone | 50 |
| Vinorelbine | 45 |
| Melphalan | 40 |
| Temozolomide | 40 |
| Doxorubicin | 39 |

TABLE 4-continued

EFFECTS OF VARIOUS AGENTS ON THE
DEATH OF PATIENT DERIVED ORGANOIDS.

| Drug Name | % Cell Death |
| --- | --- |
| Paclitaxel | 39 |
| Vinblastine | 38 |
| Cabazitaxel | 37 |
| Cisplatin | 36 |
| Etoposide | 33 |
| Trabectedine | 32 |
| Dacarbazine | 32 |
| Cyclosphosphamide | 32 |
| Carboplatin | 30 |
| Docetaxel, epirubicin, eribulin, ifosfamide, methotrexate, mitomycin, oxaliplatin, pemetrexed, vincristine | No Response |

Although the patient achieved cancer remission after being treated with the combination of GemCap and BSHE at 130 mg/day, she had extensive organ damage due to the numerous rounds of chemotherapy. She eventually died from complications due to organ damage, but it is estimated that her life was extended by about 1 year. At her death, she was free of cancerous growths. Accordingly, even though the combined therapy of chemotherapy and *cannabis* extract comprising CBD proved to be highly effective in reducing tumor growth, the pre-existing damage from chemotherapy proved to be fatal. There is no telling whether she could have achieved earlier remission had she been treated with the *cannabis* extract with CBD during earlier rounds of chemotherapy. If it were so, she would not have been subjected to the several rounds of unsuccessful chemotherapy. We can, however, confirm that her last treatment proved to be effective with a combined therapy of chemotherapy and *cannabis* extract having CBD.

Due to the success of our initial experiments and the results achieved when the live patient was treated with a *cannabis* extract with CBD, we pursued additional research with great vigor. Since our initial experiments showed a complete drop off of organoid numbers using a BSHE having a CBD dosage of about 50 μg/mL, we were interested to see how organoids responded to lower concentrations of CE. Because of the similarity and genetic profile of endometriosis and endometrial cancer, as well as the similar responses in protein signaling and responses of CB1 and CB2 receptors, both endometrial cancer based organoids and endometriosis based organoids are used to show efficacy of the CE treatment comprising CBD.

We were able to obtain tissue samples from numerous patients having different grades of endometrial cancer. Grade 1 tumors were described as having less than 5% solid non-glandular, non-squamous growth. In other words, most of the grade 1 tumors presented as having glandular and/or squamous cell likeness. In contrast, grade 2 tumors showed between 6% and 50% of solid, non-glandular, non-squamous growth, while grade 3 tumors exhibit greater than 50% of solid, non-glandular, non-squamous growth. With the number of participants and different grades of tumors, we were able to test the growth of numerous organoids at various doses of BSHE. The methods for creating organoids and experimental protocols are described below in the methods section.

For this set of experiments there were 6 different sets of each of grade 1 and grade 3 patient-derived samples, at least 9 different sets of grade 2 patient-derived samples prepared for testing BSHE at 2, 3, 4, and 5 μg/mL. Representative results were selected for graphing in FIGS. 3A, 3B, and 5A.

Figure 3A:
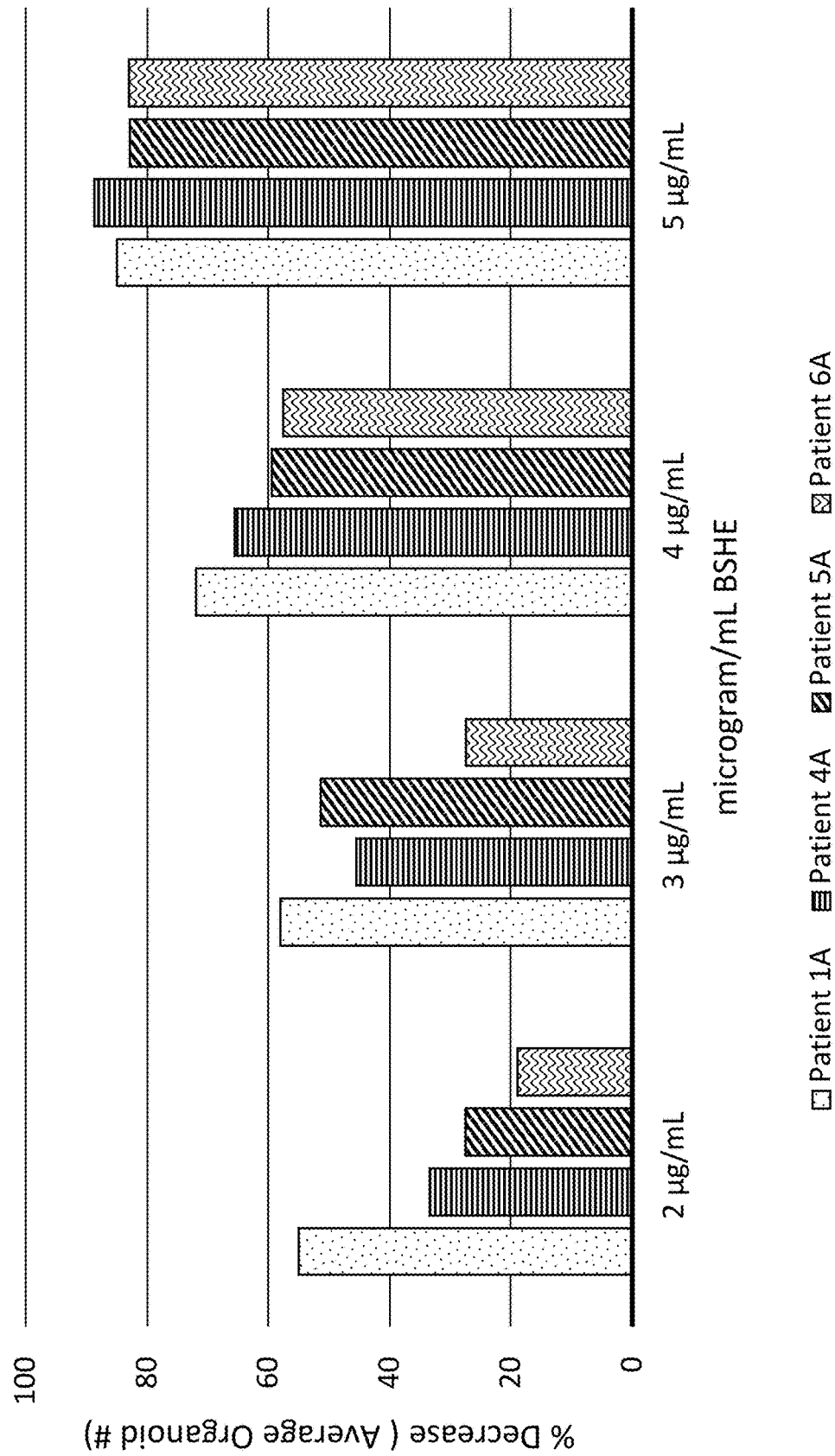
FIGS. 3A and 3B depict the decrease in in organoid number compared to the vehicle for endometrial cancer organoids treated with different concentrations of hemp extract including 2, 3, 4, and 5 µg/mL.
Figure 3B:
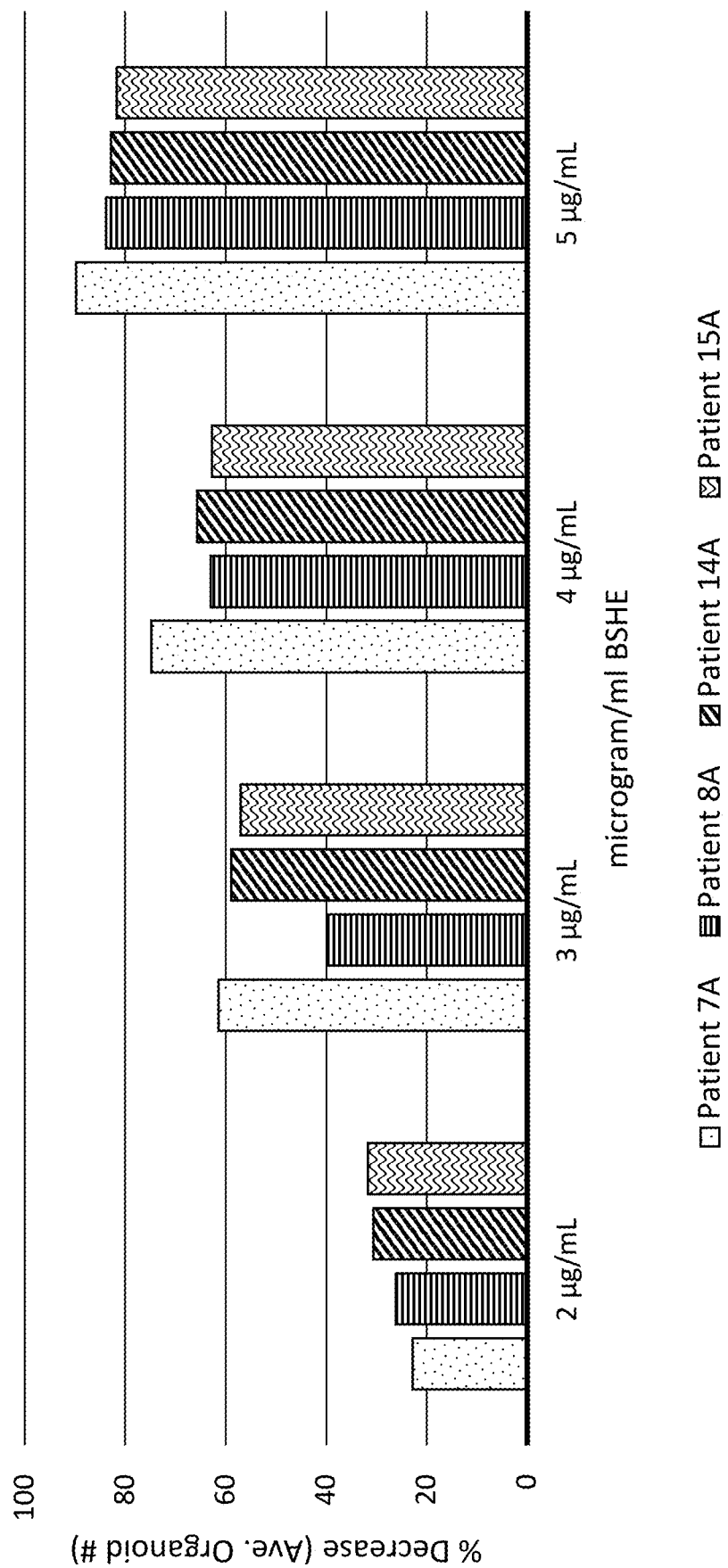
Figure 5A:
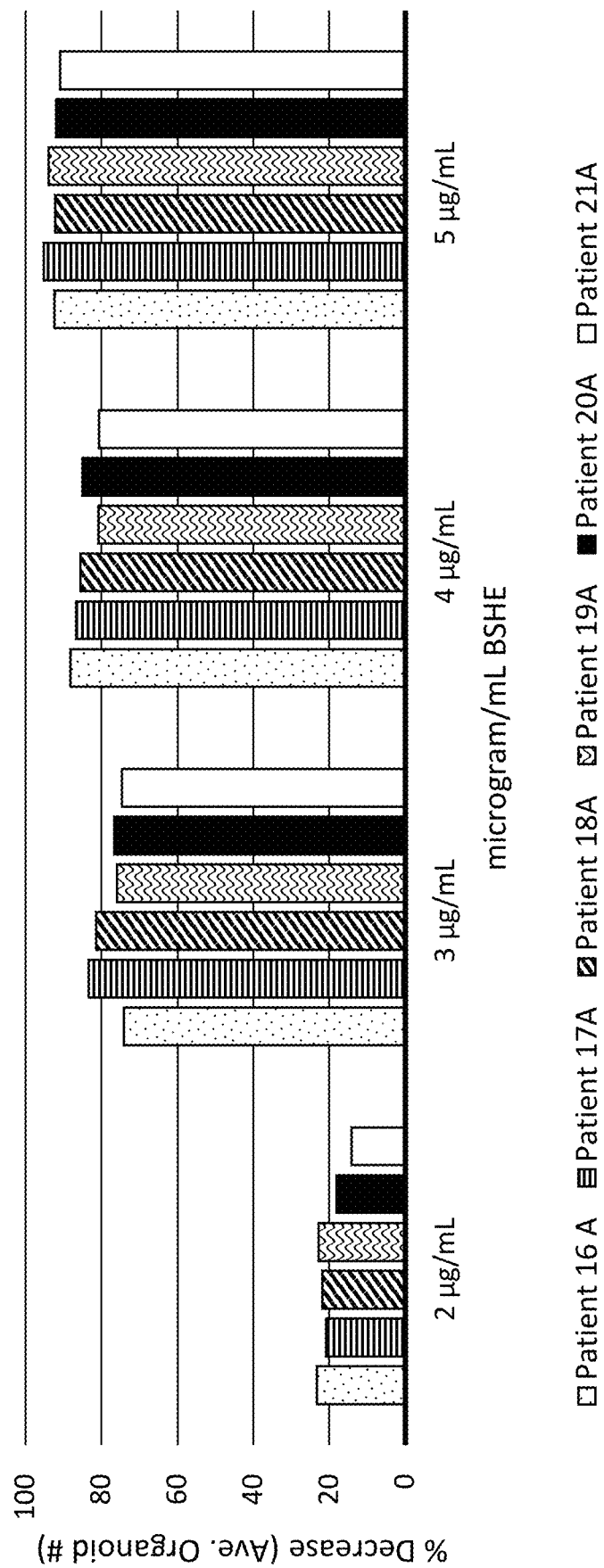
FIGS. 5A and 5B depict a grade 3 endometrial cancer organoid tested in two trials at concentrations of 2, 3, 4, 5, 7, and 10 µg/mL.

Referring to FIG. 3A, results for experiments with grade 1 endometrial cancer samples are shown as a percent decrease in average organoid number as compared to the average organoid number observed in the vehicle. Data for Patient 1A, 4A, 5A, and 6A are shown. In each case, organoid growth was inhibited at doses as low as 2 μg/mL, with cells from patient 1 being the most sensitive at this low dose such that there was a greater than 50% decrease in organoid number. For the remaining patients, a 50% decrease occurred at about 3 μg/mL to about 4 μg/mL. At 5 μg/mL, organoid formation was inhibited at least about 80%. Referring to FIG. 3B, grade 2 organoid numbers followed a similar pattern except that most grade 2 tissues showed a 50% decrease in average organoid number at about 3 μg/mL to 4 μg/mL. All samples showed about an 80% decrease in average organoid number at 5 μg/mL. Turning to FIG. 5A, surprisingly all 6 sets of samples derived from grade 3 endometrial cancer tumors showed a greater than 50% decrease in average organoid number at as low as 3 μg/mL and approached 100% decreases at 5 μg/mL. Within each grade of tumor samples individual responses to treatment with BSHE varied. Nevertheless, they all responded at the lower end of the dosing spectrum, and in most cases quite well.

Figure 4A:
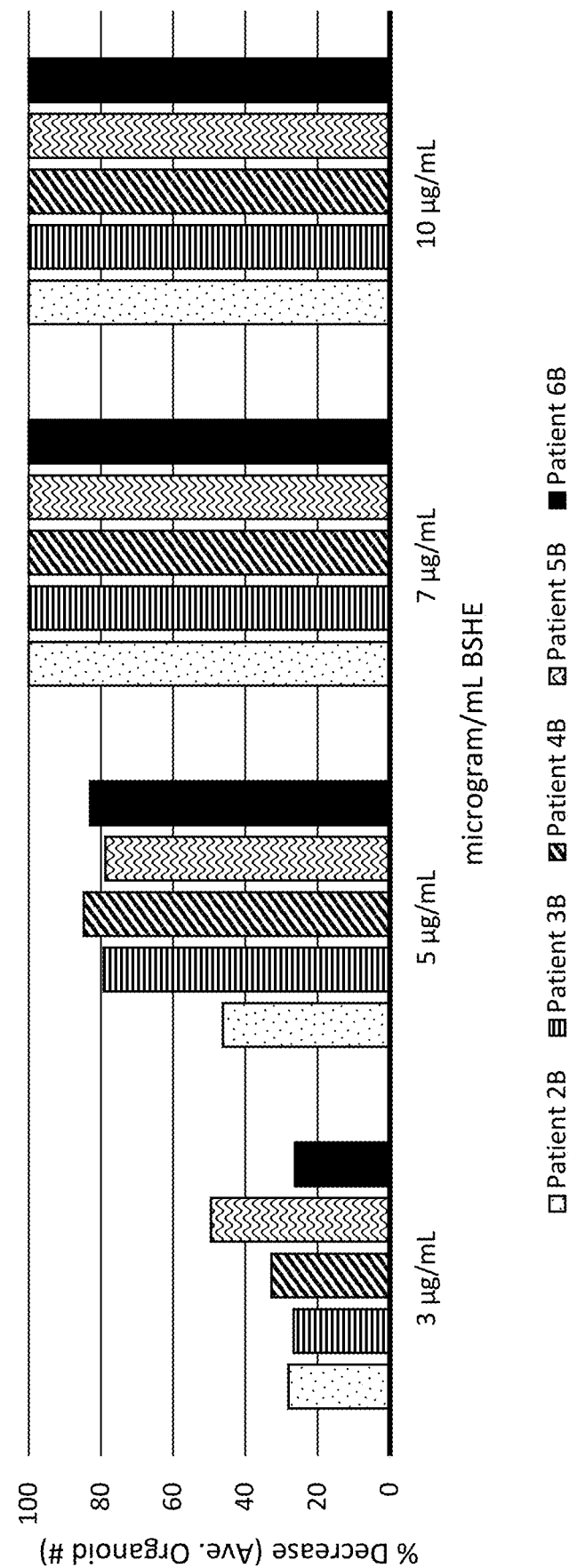
FIGS. 4A and 4B depict the decrease in in organoid number compared to the vehicle for endometrial cancer organoids treated with different concentrations of hemp extract including 3, 5, 7, and 10 µg/mL for different grades of endometrial cancer organoids.
Figure 4B:
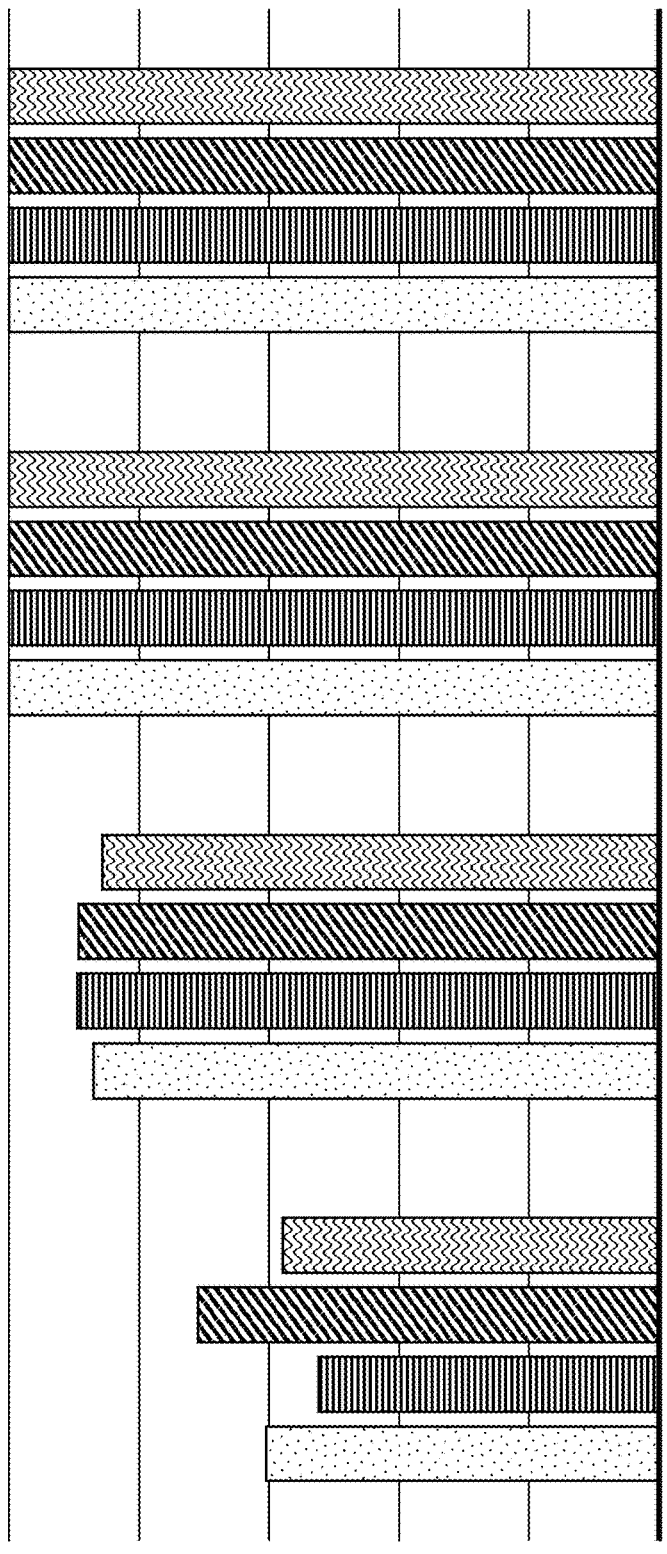
Figure 5B:
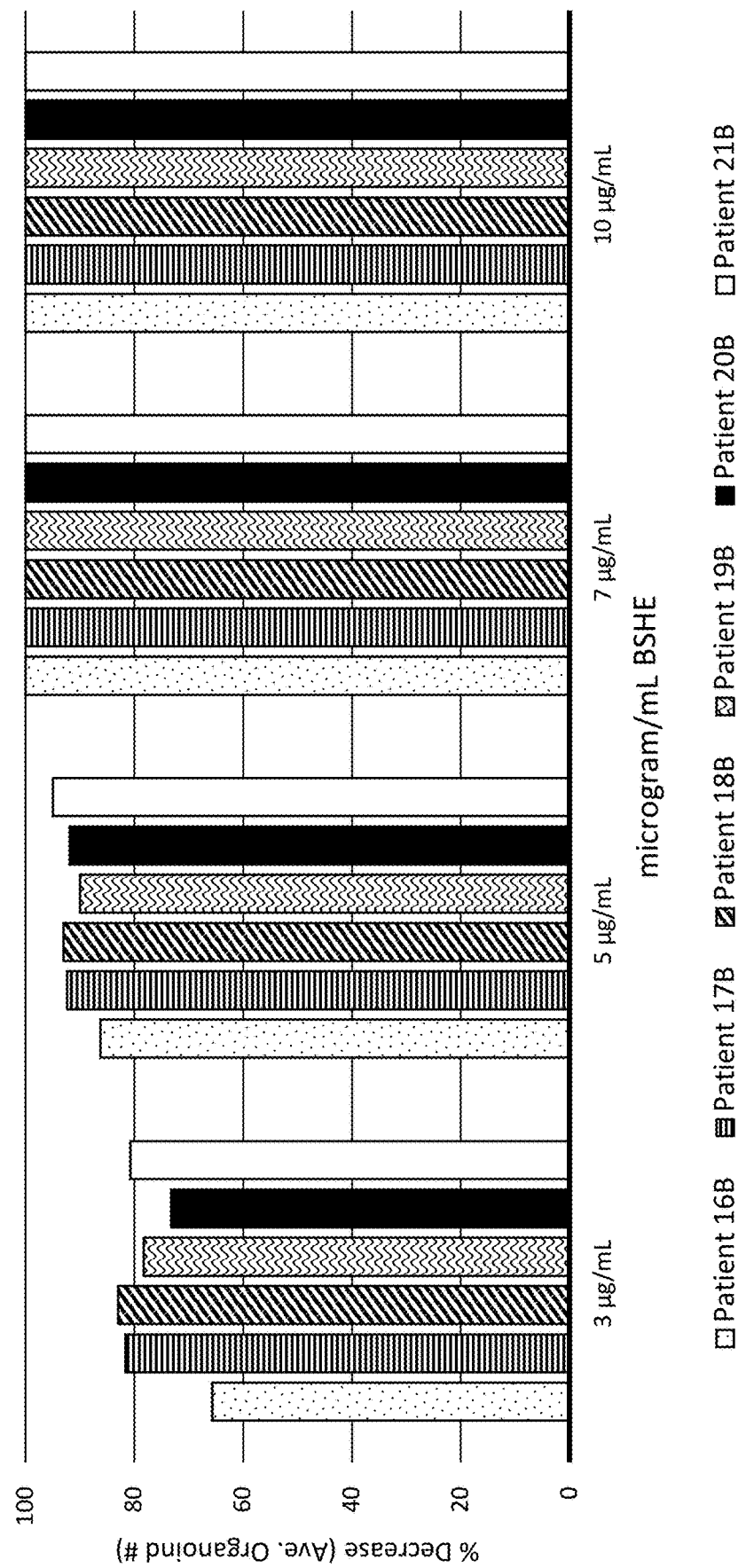

At the same time, patient-derived samples were also tested for response to 3, 5, 7, and 10 μg/mL of BSHE. Referring to FIG. 4A, representative samples of grade 1 tissues again mostly showed about a 50% decrease to the average number of organoids between 3 μg/mL and 5 μg/mL, except for cells from patient 2B. By 7 μg/mL of BSHE, however, all grade 1 patient-derived samples showed complete inhibition of organoid number, even patient 2B. Referring to FIG. 4B, surprisingly, grade 2 samples in this set were affected by 3 μg/mL BSHE such that, of the representative samples shown, all four had about a 50% or greater decrease in average organoid number. Again, at 5 μg/mL the response was a greater than 80% decrease, with 100% inhibition of organoid formation at 7 μg/mL BSHE. Referring to FIG. 5B, the grade 3 patient-derived samples in this set also were surprisingly sensitive to low doses of BSHE with a 50% decrease in average organoid number for all patient samples being less than 3 μg/mL. A 5 μg/mL dosage of BSHE again showed a greater than 80% decrease in the average organoid number and at 7 μg/mL there were no organoids.

Accordingly, based on FIGS. 3A, 3B, 4A, 4B, 5A, and 5B, organoids from grade 1, 2, and 3 EC were able to show a dramatic reduction in the average number of organoids as compared to the vehicle at concentrations as low as 2 μg/mL, and in each case, as low as 7 μg/mL. Therefore, application of *cannabis* extracts comprising CBD at the defined concentrations of CBD are effective decreasing the number of viable patient derived organoids from EC. The data is clear that the given doses of *cannabis* extracts, with a known quantity of CBD are effective in reducing endometrial cancer organoid growth.

After narrowing down the range in which 50% of endometrial cancer organoids were inhibited from forming in the presence of BSHE, we then turned to other *cannabis* extracts comprising CBE to determine their efficacy in inhibiting cancerous organoid formation. Thus, in addition to retesting broad spectrum hemp extract (BSHE), which was the basis for all prior studies, we also tested a full spectrum hemp extract (FSHE), which typically contains less than 0.3% of $\Delta^9$-THC, an isolated CBD, which is a naturally derived and isolated CBD, and finally an isolated CBDA, which is a precursor to CBD. These *cannabis* extracts were then tested against endometrial based organoids, which confirm the efficacy across the different cells, both in the endometrial cancer based organoids as well as in the endometriosis based organoids.

FIG. 6A depicts tests for % viability on endometriosis based organoids at 0, 1, 2, 3, 4, 5, 7, and 10 μg/mL after being treated with BSHE, FSHE, and CBD isolate. The data here, surprisingly show that each of the organoids are completely treated by doses as low as 5 μg/mL for CBD isolate, as well as at 7 μg/mL for both the BSHE and the CBD isolate, and finally at 10 μg/mL for all three of the compounds tested in FIG. 6A. This data falls in line with the results seen in all prior studies tested on the endometrial cancer organoids.

FIG. 6B then tests the same endometrial based organoids with a CBDA isolate. Here, slightly higher concentrations were required to reach below 10% viability. Less than 10% viability is considered 95-100% cell death in these experiments due to residual signaling from dead cells and Matrigel. We see a little less than 50% viability beginning at 15 μg/mL and then rapidly decreasing to below 10% viability by 25 μg/mL, with a complete resolution at 50 μg/mL. However, these studies confirm that the efficacy of the CE comprising CBD was conserved over different grades of endometrial cancer and also to endometriosis based organoids.

To further our studies on the effects of *cannabis* extracts comprising CBD, we looked at endometrial cancer tumor volume in mice. Mouse studies are useful to take cell-based applications and confirm their efficacy in a whole animal system. Furthermore, the mice allow for testing of systemic delivery of the drugs. FIG. 7 depicts the results over the 21-day period of testing with administration of 30 mg/kg of four different CBD types. The mice tests were performed according to the protocol in the method section, below.

Generally, EC stem cells from the same patients that participated in the organoid studies for endometrial cancer, were injected into the mice, and allowed to grow. After tumors reached a certain size, the mice were either injected (3 times/week) with the extract-delivery vehicle or with the particular *cannabis* extract. After a certain amount of time elapsed, tumor size was measured. The details regarding patient-derived xenograft methodology and experimental protocol are provided in the Methods section.

Referring to FIG. 7, the number of days of treatment is plotted against an % change in tumor volume for each of the vehicle, BSHE, FSHE, CBD isolate, and CBDA. The % change is an average number taken from tumor volumes of three mice compared to the starting average tumor volume on day 0 of treatment. Change can either be positive (tumor increases in size) or negative (tumor decreases in size). As expected, the vehicle (no treatment control) continuously increased in size over 21 days with almost a 150% increase from the day treatment started. In contrast, tumors in mice treated with a *cannabis* extract comprising CBD decreased in size. Thus, at the very least we have shown that systemic delivery of *cannabis* extracts comprising CBD is can be used to treat endometrial cancer. This is an important verification as it confirms bioavailability of the various *cannabis* extracts comprising CBD.

Successful delivery of the various *cannabis* extracts comprising CBD, however, is validated by the observed changes in tumor volume. For example, after one week of treatment (i.e., 3 doses of about 30 mg/kg extract) all tumor averages indicate an initial increase in size. By day 10, however, most average tumor volumes began to decrease with the tumors in mice treated with CBDA showing the greatest decrease over the three days of from a little over a 30% increase to a greater than 30% decrease; an overall decrease that is greater than 60% in just three days. Mice treated with BSHE and FSHE showed a similar switch from an increase in average tumor volume to a decrease average tumor volume, but not as dramatic as that observed with CBDA. Interestingly, the tumors in mice treated with CBD isolate were not as responsive as the tumors in mice treated with the other *cannabis* extracts, which is especially surprising as CBDA is a precursor to CBD. Within 2 weeks (14 days-6 doses total), most tumors were at least 50% decreased in volume compared to their starting size, except for those in the mice treated with CBD, which was less than 50%, but still a decrease in average tumor volumes. In contrast, mice treated with CBDA showed an average decrease in tumor volume of 70% compared to starting tumor volume averages. By day 21, only three weeks of treatment, 9 doses total, average tumor volume in each of the treatment groups were decreased by at least 50%, with those treated with CBDA approaching 100% resolution. What is even more amazing is that when left untreated, the average tumor volume was slightly less than a 150% increase. Thus, the *cannabis* extracts comprising CBD not only prevented endometrial tumor volume from increasing, but they also reversed tumor volume, in some cases almost completely. These results confirm what was observed in the organoid experiments and what was observed in the human patient that was treated with CE.

Notably, the concentrations of *cannabis* extracts comprising CBD used in the mouse model experiments is on the low end of what would be considered a therapeutic dose for administering to a human patient or a mouse. For example, the 30 mg/kg given to the mice translates to about 170 mg for an average human female. Recall that a CBD isolate is currently prescribed in the US at a concentration of 5-50 mg/kg daily. We intentionally used low doses to treat mice to show the impact of various *cannabis* extracts comprising CBD at these low doses on tumor volume over time rather than forcing the data to zero, by using double, triple, or higher of the dose as administered to the mice, each of which would be appropriate human equivalent doses. Furthermore, even with the lower dosing, within 3 weeks of treatment, virtually all of the samples had tumor volumes progressing toward zero, especially those treated with CBDA. Therefore, when comparing dosages used in the mice to those applied to the organoids, we saw that each sample in the mice retained the efficacy from the organoid data. In other words, endometrial cancer cells obtained from the same patient were responsive to *cannabis* extracts comprising CBD in both an organoid form and patient-derived xenograft form. As such, administering higher doses of *cannabis* extracts comprising CBD, will yield a greater reduction in tumor volume in the mouse model. From all of these experiments taken in total, it is quite clear that, administering *cannabis* extracts comprising CBD is effective in greatly decreasing the volume of endometrial cancer tumors, which not only slows the growth of endometrial cancer tumors, but may eradication of tumor cells together, as is demonstrated in our mouse models. Similarly, efficacy in endometriosis and NCGD's are confirmed by these studies. Therefore, a new methodology for treating the NCGD, such as endometriosis is provided.

Figure 1F:

Moreover, we have shown that gynecological tissues can be targeted by certain applications of *cannabis* extract comprising CBD, whether through oral, oral mucosal, vaginal mucosal, or other administration to treat EC and reduce tumor size. Because of the targeted approach toward gynecological tissues, those of ordinary skill in the art will recognize that certain therapeutics are able to pass through the vaginal mucosa and contact tissues both on the vaginal wall, but also tissues adjacent to the vaginal wall, including the entirety of the gynecological tract, including the uterus, cervix, ovaries, etc., as non-limiting tissues. Indeed, while these tissues are generally connected, application into the vagina does not always ensure that a therapeutic will also travel to and impact the uterus or ovaries. However, there is an abundance of endocannabinoid receptors in the female reproductive tract to allow for possible therapeutic impact of administered cannabinoids to such tissues, as is depicted in FIGS. 1E and 1F. Furthermore, intravaginal delivery of cannabinoids may result in uptake via the inguinal lymph nodes, leading to addition systemic uptake from the reproductive tract.

It is also critically important the CE compositions are able to treat the patient without significant damage to surrounding and other healthy cells. This is equally true when administering chemotherapy in a cancer patient as it is in treating the noncancerous disorders detailed herein, with a CE comprising CBD as detailed herein.

Figure 8A:
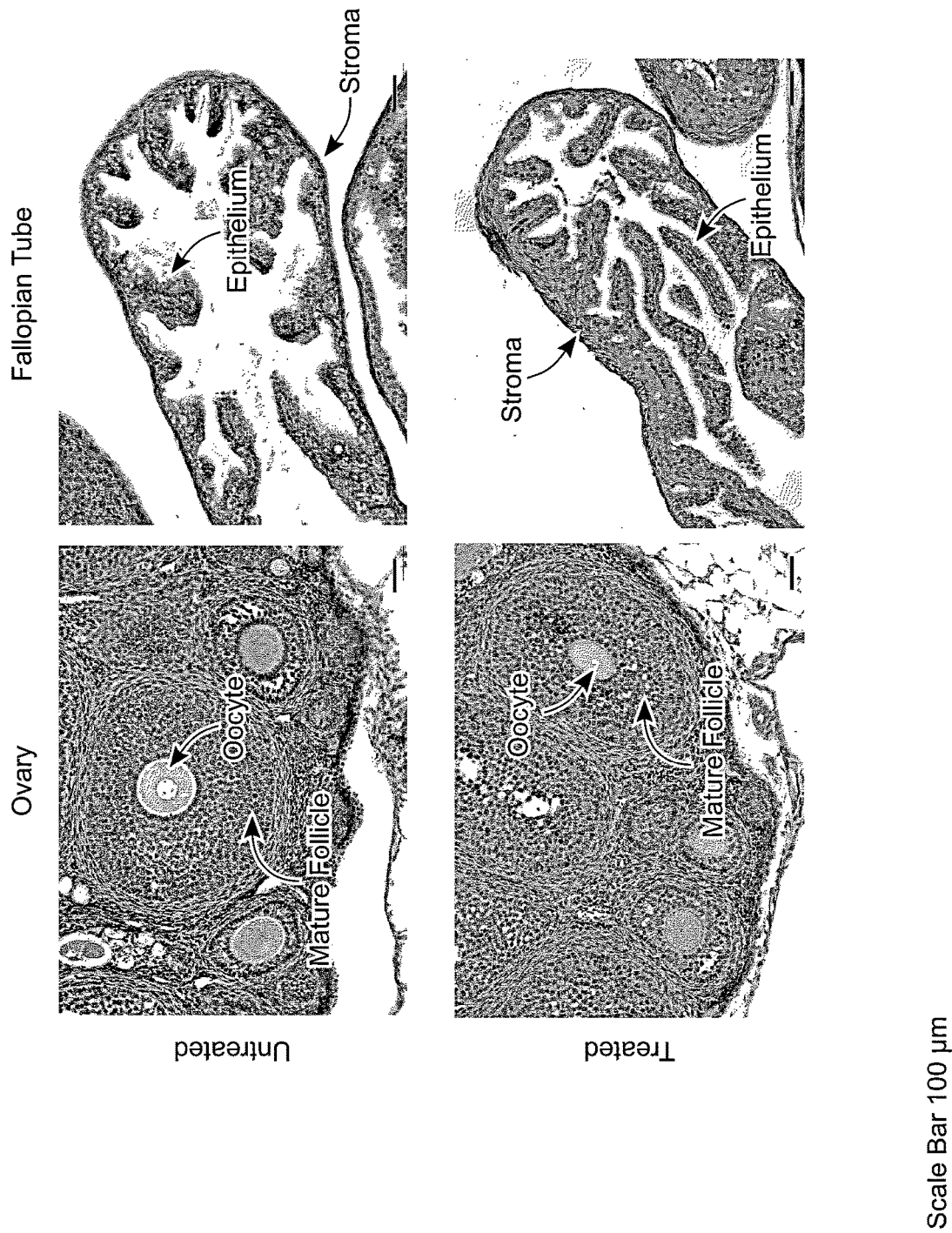
FIGS. 8A and 8B depicts images of a histopathology performed on mouse tissues treated with *cannabis* extract and depicting that therapeutic treatment with the *cannabis* extracts does not damage the normal reproductive tract cells.
Figure 8B:
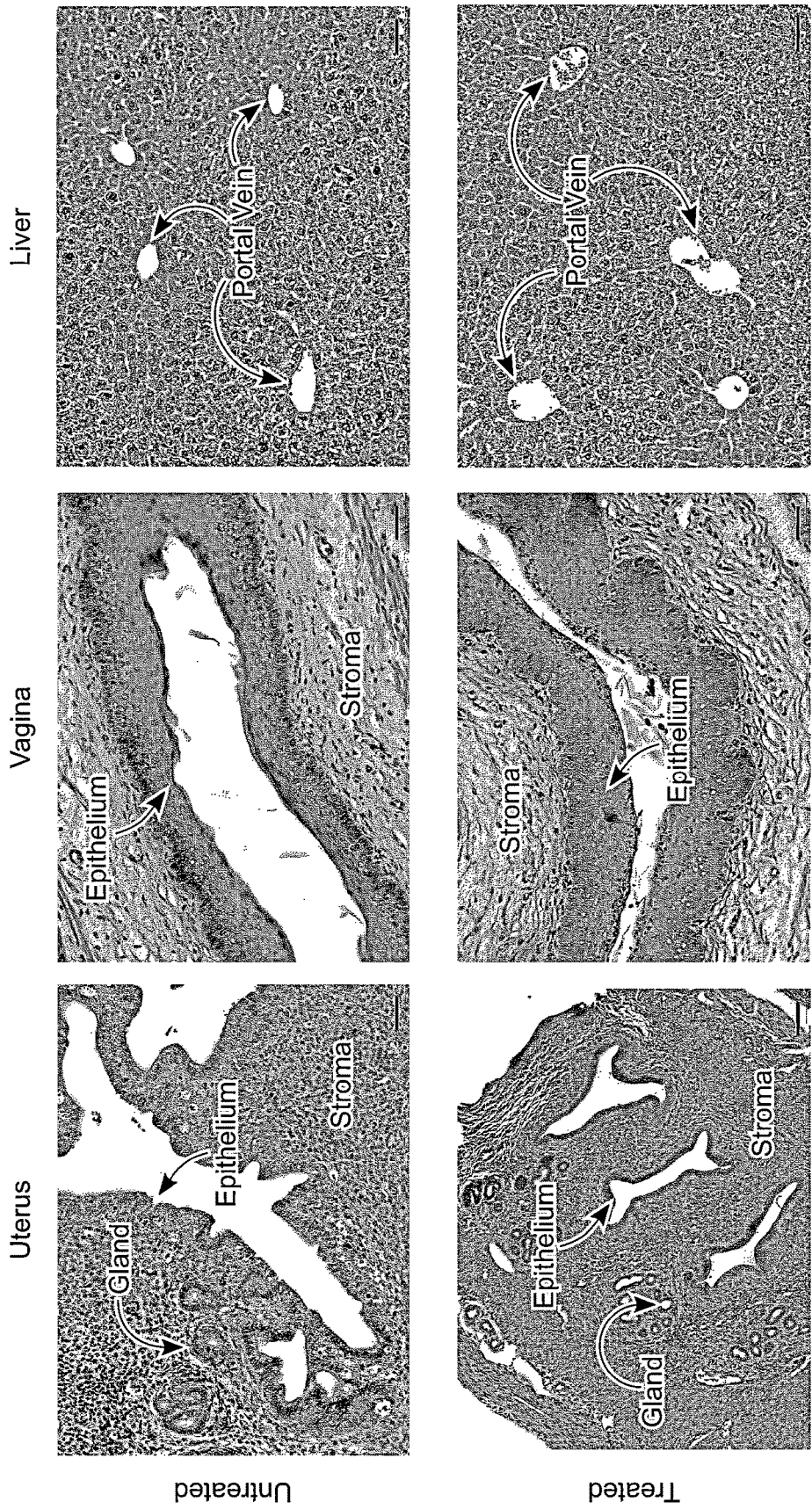

*Cannabis* extracts such as the ones used in our studies did not damage or adversely affect tissues of mice used in the patient-derived xenograft experiments. For example, FIG. 8 compares histological tissue samples taken from the mice treated with a *cannabis* extract comprising CBD and healthy mouse tissue. FIG. 8A shows untreated and treated samples from ovaries and fallopian tubes. Chemotherapies are known to adversely affect oocytes and follicles. Here, the treated mice have mature oocytes and follicles that are both healthy. Likewise, healthy epithelial tissue is also known to be damaged by chemotherapy, often leading to severe organ/ organ system damage that may be fatal. In comparing the untreated and treated epithelial tissue in mouse fallopian tube, both appear to be healthy. Similarly, tissues from treated and untreated mouse uteri, vaginas, and liver are compared in FIG. 8B. The liver is especially telling when damaged by chemotherapy. As can be seen in FIG. 8B, the liver samples are virtually identical. This is critically important, as treatment with high doses of chemotherapy are indiscriminate and damage these cells, when given over time. Thus, reduction in the quantity of chemotherapy drugs, whether at lower doses or none, in combination with the *cannabis* extract can improve the outcome for patients by decreasing tumor volume at a greater rate, reducing the tumor volume to a greater total percentage than chemotherapy alone, and does not otherwise cause damage to the corresponding, healthy tissues of the reproductive tract and the liver as would occur from chemotherapy use. CBD is non-toxic in non-transformed cells and does not affect physiological parameters (heart rate, blood pressure and body temperature), gastrointestinal transit or psychomotor or psychological functions. Chronic use and doses up to 1,500 mg/day of CBD are established as well tolerated in humans.

Moreover, CBD dominant *cannabis* extracts have no potential for abuse or dependence. This was best highlighted during the World Health Organization's 41$^{st}$ Expert Committee on Drug Dependence held in Geneva, Switzerland in November 2018. Annex 1 from the meeting's report states "cannabidiol should not be scheduled within the International Drug Control Conventions. Cannabidiol is found in *cannabis* and *cannabis* resin but does not have psychoactive properties and has no potential for abuse and no potential to produce dependence. It does not have significant ill-effects."

Figure 9:
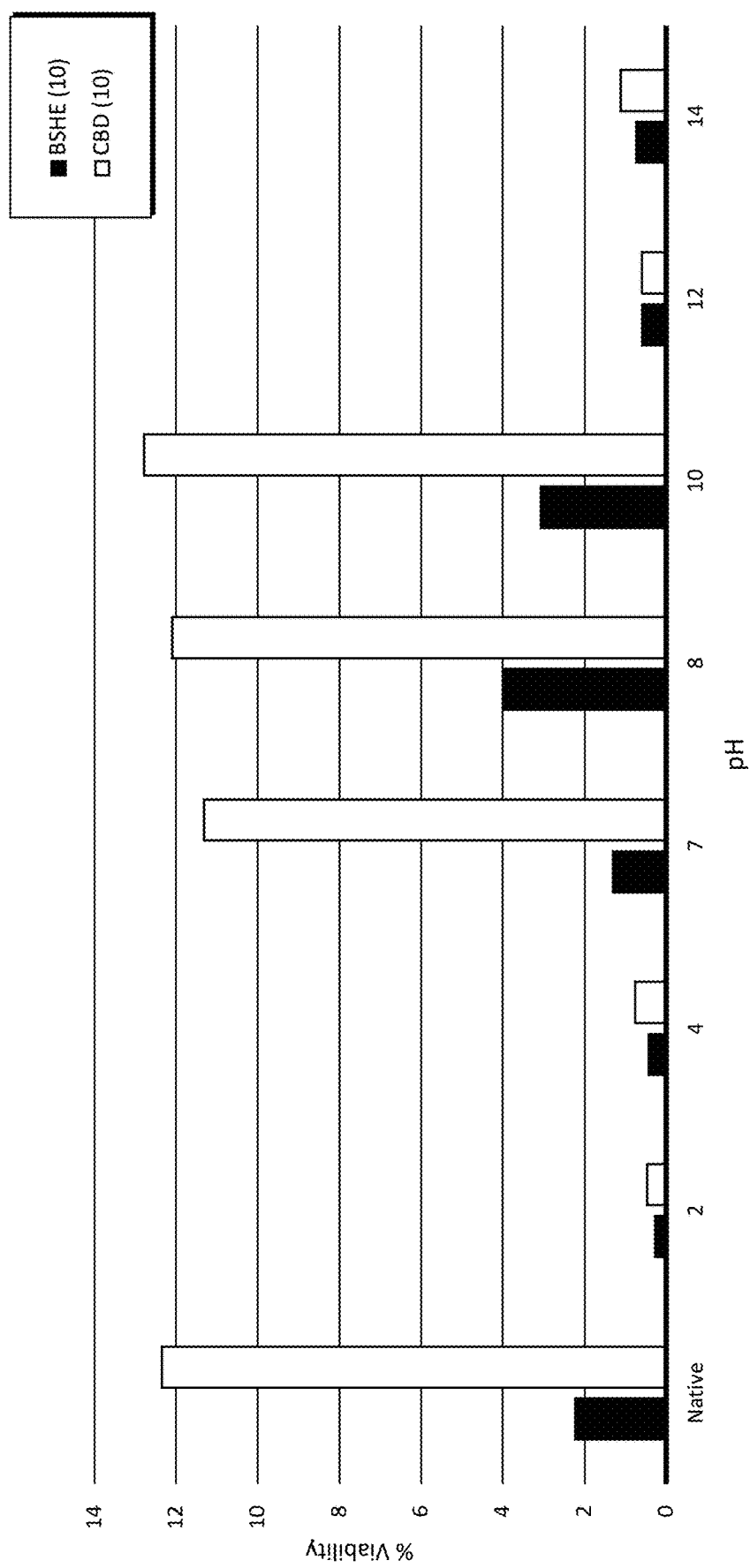
FIG. 9 depicts a chart showing the impacts of pH on therapeutic efficacy of the *cannabis* extracts.

A further interesting observation was made by looking at the impact of pH on the efficacy of *cannabis* extracts comprising CBD on the viability of organoids. Referring to FIG. 9, the % of viable organoids as a function of pH and BSHE and CBD isolate treatment, each at 10 µg/mL is show. In this set of experiments, organoids were derived from ovarian cancer tissue. Interestingly, the carrier alone did not destroy the organoids, and so the data is not depicted. At an extract's native pH, organoid production in the presence of 10 µg/mL BSHE was limited to about 2% and in the presence of the same amount of CBD isolate it was about 12%. However, increasing the pH led to substantial improvements in efficacy as is shown at the pH of 12 and 14. At this end of the pH scale substances tend to be corrosive, and at a pH of 14 are highly corrosive, alkaline concentrations that are not suitable for therapeutic use. Indeed, such a pH would not be isotonic, nor would it be appropriate for intravaginal application. The vagina has an acidic pH, which is necessary to maintain the balance of bacteria. However, strong modifications of the pH may lead to denaturing of the proteins or other problems. What was immediately evident is that the first attempts to buffer, even slightly, the pH to be more acidic, yielded worse results. Indeed, each of the two *cannabis* extracts examined in this test had less efficacy by decreasing pH from 10.5 to pH of about 10. Furthermore, reducing the pH to 8 again made the BSHE almost twice as weak at killing the organoids as the native pH, while the CBD isolate shows virtually no change. Even at pH of 7, a neutral pH, the changes are minimal at best.

In such a situation, decreasing the pH further would not likely lead to any further gains for therapeutic efficacy, as the changes were typically worse or virtually no change as compared to native pH. Instead, by further decreasing the pH to 4, a dramatic improvement in the % viability was seen for each of the BSHE and the CBD isolate, such that each were under a 1% viability, which was unexpected based on the prior data trending toward a worse response or virtually unchanged response. Accordingly, when providing the *cannabis* extract, especially where the *cannabis* extract is provided intravaginally or oromucosally, utilize a buffer to modify pH to between 2 and 6, yields a superior response compared to giving the *cannabis* extract at its native pH. Preferably, the *cannabis* extract is provided in a carrier with a pH of between 3.5 and 5.5, and more preferably at between a pH of between 4 and 5.

Summary of Patient Samples

The use of organoids to test the therapy is exciting as we can use representative cells to determine response to different therapies, instead of relying on analog models in other species. Accordingly, the results show that upon contact with the BSHE or FSHE comprising CBD, the organoids were destroyed across varying concentrations, but frequently as low as 5, 7, 10, or 20 µg/mL. This was shown in several different patients of varying stages and grades of endometrial cancer and endometriosis based organoids, all with the same success rates. Converting these numbers into mouse models, confirmed the same efficacy, wherein tumor growth was arrested and tumor volume was reduced, across the board.

Intravaginal delivery is well studied and considered safe, effective and well tolerated. Intravaginal delivery avoids gastrointestinal absorption and bypasses first pass metabolism, while facilitating a localized effect and a steady, sustained therapeutic response. Absorption and systemic delivery via vaginal epithelium occurs rapidly with similar lipophilic compounds. Variances in thickness of the vaginal epithelium and vagina fluid characteristics, including pH, presence of cervical mucous, and microbiota, may influence absorption rates and bioavailability.

Rectal suppository delivery results in an increased bioavailability (51-60%) versus oral routes for CBD. Data on oromucosal or sublingual delivery, demonstrates that CBD has a maximum plasma concentration of 1.6 hours, but this can be delayed in some individuals. Oral CBD has a maximum plasma concentration of about 2.5-5 hours but can be delayed up to 6 hours for some individuals. Coadministration with high fat food has been shown to increase Cmax by up to 5-fold concentration. Delivery of CBD via highly vascularized nasal mucosa results in rapid uptake and a Tmax of approximately 10 minutes. The vaginal mucosa, however, has not yet been utilized for therapeutic treatments. Accordingly, CBD uptake through intravaginal absorption is remains an opportunistic route for administration as detailed herein.

Accordingly, mucosal dosing, particularly intravaginal dosing has a therapeutic efficacy that can allow for targeted treatment of EC cells, which will treat both localized tumors as well as metastasized tumors. These data were confirmed by further testing within human patients, which showed that treatment with CBD was effective in reducing chemoresistant EC, which had metastasized, in the body.

Methods and Calculations

Patient-Derived Organoids

Patient derived organoids were created by collecting endometrial cancer tissue samples after surgery. The collected tissue was bathed, on ice, in Hank's Balanced Salt Solution (HBSS) (Hyclone, SH30031.02) with 1% Penicillin/Streptomycin (P/S) (Life Technologies, 15070-063). The tissue sample was washed three times with Dulbecco's phosphate-buffered saline (DPBS) and 1% P/S on a shaker (70 rpm) for 15 minutes each wash. Thereafter, the tissue sample was finely minced with a sterile blade while in a pre-sterilized cell-culture hood. All minced parts were enzymatically digested (Accumax™—Innovative Cell Technologies Inc., AM105-500) for about 2.5 hours at room temperature. After 2.5-hours, the whole digested tissue mince was transferred for further enzyme digestion with TrypLE™ express, (Gibco, 12604-021) for another 45 minutes in a 37° C. water bath. During this time, the solution was continuously agitated in 5 minutes intervals. Thereafter, the solution of digested tissue was passed through a 70 µm filter on a 50 mL falcon tube. The filter was removed and the flow-through with the cells was collected in 5% FBS AD+++ medium (comprising 1% ITS, 2% B27, 1% N2, 25% WRN, hegf-50 ng/mL, hfgf-10-100 ng/mL, Nicotinamide-1 mM, N-acetyl cysteine-1.25 mM, Primocin-0.2%, Estrogen-2 nm, A8301-0.5 µM, and Y27632). This cell suspension was centrifuged at 1000 rpm for 5 minutes at room temperature to get a cell pellet for counting. Upon checking under hemocytometer cell number was calculated and processed for organoid culture. Final cell suspensions were checked under a microscope for RBC contamination and if found, the RBCs were lysed used Red Blood Cell Lysis Buffer (Roche Diagnostics, 11814389001). The resultant endometrial cancer cells from a human patient were grown and maintained in a humidified chamber at 37° C. with 5% $CO_2$.

Organoids derived from ascites samples were treated somewhat differently; the ascites fluid was centrifuged at 1000 rpm for 10 minutes at room temperature to get a cell suspension. The cell suspension was then treated with Red Blood Cell Lysis Buffer (Roche Diagnostics, 11814389001) to remove the RBC from the final cell suspension.

To culture patient-derived organoids, 2-3×10^3 cells were plated in a pre-warmed (37° C.) 96-well plate in 10 µL of Matrigel (5% FBS AD+++ medium) per well. Individual patient cell organoids were cultured separately in different plates. Individual patient cells were handled separately to reduce the chance of cross-contamination. After mixing cells with Matrigel, 10 µL droplets were placed in wells and put in a 37° C. incubator with 5% $CO_2$ for 30 minutes. Upon solidification of the Matrigel droplet with cells inside, the plate was placed inside a sterile hood and immersed the Matrigel droplet in 200 µL of organoid growth media. Cells were allowed to grow into mature organoids for 14 days. Treatment with individual CBD agents (Broad Spectrum, Full Spectrum, CBD Isolate, and CBDA) or in combination with chemotherapeutic agents (Paclitaxel or Carboplatin) was usually started on day 5, where the individual drug or drug combinations were added in the growth medium. All treatments were done in triplicate, including vehicle-only controls (Dimethyl sulfoxide in culture medium at the highest concentration used for drug treatments).

Some human equivalent doses were calculated using a standard formula: (M=m/MW×1/N where m=mass in grams, MW=molecular weight of the substance and V=volume of the diluent in liters). For example, if organoids are dosed with 54.35 µM Drug X, 0.0032 mg of Drug X are needed in 100 µL or 0.0001 L (V) of solute. That is equivalent to 0.00005435 M or 54.35 µM concentration, where the MW of Drug X=588.72 g/mol and m=0.0000032 g.

When using the 96 well plates, the following formula is used for translating the given dose to a human dosage. The surface area of a single well in a 96 well plates is 0.32 cm². Thus, the clinical dose equivalent (mg/m²) is 100 mg/m² by following the formula: Clinical Dosage (mg/m²)=(PDO dosage in mg/culture plate surface area cm²)×1002. When comparing the two different methods of translating the organoid dose to the human dose, the two calculations show a similar human equivalent dose, for example of approximately 200 mg/day for the organoid equivalent of 10 µg/mL.

The IC50 is the 50% inhibitory concentration which is conventionally used to determine drug potency with cell-based cytotoxicity tests. To determine the IC50 for specific patient-derived organoids, individual patient organoids were treated with each of BSHE, FSHE, CBD Isolate, and CBDA as described above. Results of such treatment were used to find individual IC50s by using least squares regression (in Graphpad Prism 9) on inhibitor (i.e., a particular *cannabis* extract) vs normalized response-variable slopes. Thus, an IC50 was determined for each cannabinoid extract and selected patient-derived organoids. Thereafter, for each of the patient-derived organoids selected for testing a *cannabis* extract with CBD in combination with a chemotherapeutic agent, the organoids were treated with either the chemotherapeutic agent alone, or the chemotherapeutic agent in combination with a dosage of the cannabinoid extract equivalent to the calculated IC50 for the particular extract/organoid combination. The same IC50 dose was given with each incremental dose of chemotherapeutic agent. Notably, the doses given for each chemotherapeutic agent in the organoids are below an equivalent of a maximal doses suitable for human administration. In this way, we could determine if a specific IC50 of a given *cannabis* extract comprising CBD and a reduced amount of chemotherapeutic agent (Paclitaxel, Doxorubicin or Carboplatin) could be used to obtain the same amount of cancer cell death as of a standard human dose of a chemotherapeutic agent.

Cell Viability Assay

To assess the cell viability in organoids after treatment, CellTiter-Glo® Luminescent Assay (Promega #G7572) was used. In brief, on day 14 of organoid culture, the Matrigel droplet in each well with organoid inside was immersed in 100 μL of fresh growth media and 100 μL of CellTiter-Glo® reagent following the manufacturer's guideline. Blank wells containing only media and CellTiter Glo® reagent (no cells) were also included in each plate. Then the plates were put on a shaker @ 110 rpm at room temperature for 5 minutes to induce cell lysis, followed by 25 minutes at room temperature to stabilize the luminescent signal. Each step after adding the CellTiter Glo® reagent was performed in the dark. Luminescence was measured on a FLUOstar OPTIMA plate reader (BMG Lab technologies, Offenburg, Germany). Analysis was performed by normalizing treatment values to the vehicle control and plotting them as a percentage of the vehicle control. Drug IC50 values were determined by inhibitor vs normalized response-variable slope using least squares regression in Graphpad Prism 9.

Patient-Derived Xenograft (PDX) Mouse Generation

Human patient cells from endometrial cancer were injected subcutaneously into female NOD/SCID gamma mice after resuspending in 100 μL solution. Once the tumor grew to a visible size all mice were intraperitoneally injected with single *cannabis* extract comprising CBD agent using the extract alone at 10-30 mg/kg body weight or the *cannabis* extract comprising CBD agent together with a given chemotherapeutics where the given *cannabis* extract was given at 10-30 mg/kg body weight, Paclitaxel was given at up to 20 mg/kg body weight or the vehicle thrice per week for up to 5 weeks. Tumor size was measured before treatment, followed by twice a week measurements. All treatment group mice were kept alive for up to 10 weeks after drug injection or until the tumor volume grows bigger than 2500 mm$^3$.

Tumor size was measured along with body weight at the time of tissue collection. All tumor tissues were removed carefully from the euthanized mouse body. Tumor tissue samples were kept for histology, proteomics, genomics, and other downstream processing. All downstream processing was completed following NCI Patient-Derived Models Repository SOPs.

Mouse PDX to Human Dose Conversion

The Food and Drug Administration (FDA) has suggested that the extrapolation of animal dose to human dose is correctly performed only through normalization to body surface area (BSA), which often is represented in mg/m$^2$. The human equivalent doses (HEDs) can be more appropriately calculated by using the formula: Human Equivalent Dosage in mg/kg=Mice Dosage (mg/kg)×(Mice $K_m$/Human $K_m$). The correction factor ($K_m$) is estimated by dividing the average body weight (kg) of species to its body surface area (m$^2$). For example, the average human body weight is 60 kg, and the body surface area is 1.62 m$^2$. Therefore, the $K_m$ factor for human is calculated by dividing 60 by 1.62, which is 37 and same way the mouse $K_m$ factor was calculated, which is 3. Now to interchange of unit (mg/kg to mg/m$^2$) of dose of animals or human is carried out using the $K_m$ factor as per BSA: Dosage for mg/m$^2$=$K_m$×dosage in mg/kg.

Embodiments

In preferred embodiments, a CE comprises between 50 to 95% CBD. Accordingly, a 10 mg dose of CE comprises between 5 to 9 mg of CBD. The remaining components of the CE comprise additional cannabinoids, terpenes, polyphenols, essential fatty acids, and phytonutrients. A pharmaceutical composition herein comprises a CE, which makes up between 1 and 99% by weight of the composition. When provided in a pharmaceutical composition, the concentration of CBD is typically given as a dose at between 5 and 50 mg/mL of a pharmaceutical composition. Certain compositions comprise additional excipients and ingredients, including but not limited to a fat, an oil, MCT oil, long chain triglyceride oils, very long chain triglyceride oils. Terpene components including but not limited to β-myrcene, β-caryophyllene, linalool, α-pinene, citral, D-limonene, eucalyptol. Polyphenols may include, but are not limited to catechins, quercetin, cannflavin A/B/C, rutin, and chlorogenic acid. Omega 3, omega 6, and omega 9 fatty acids may be present, as well as additional phytonutrients such as tocopherol, sterols, carotene, aliphatic alcohols, and certain minerals. These components, including the carrier may make up to 99.9% by weight of the pharmaceutical composition, however, more preferably the CE, comprising CBD comprises between 1 and 99% of the pharmaceutical composition, and preferably between 40 and 99% by weight of the composition.

Therefore, a preferred embodiment is related to a method of treatment of endometriosis comprising, administering to a patient an effective amount of a pharmaceutically acceptable composition comprising CBD, wherein the composition comprises a CE, such as a BSHE or FSHE. In preferred embodiments, an effective amount is one effective to generate a concentration of at least 10 μg/mL of the BSHE or FSHE at the target tissue, and more preferably at least a target concentration of at least 20 μg/mL. In a further preferred embodiment, an effective dose is between 10 and 4250 mg a day of CBD, wherein said CBD is provided in a CE through a mucosal application, such as intravaginal, oromucosal/sublingual, nasal, or rectal. The methods for treatment herein are effective in eliminating inappropriate lesions, i.e., cells that have migrated from their intended location in the body. Furthermore, these methods stop or retard growth of the endometrial cells outside of the endometrium, without harming the endometrium. Furthermore, the methods herein limit or eliminate migration of endometrial cells outside of the endometrium, and finally for control of symptoms, including the reduction of pain, bleeding, and formation of endometriomas and fibrous tissues that lead to scar tissue development and adhesions.

In a further embodiment, the method of treatment may be to relieve and treat an ovarian endometrioma or a deep endometriosis. In further embodiments, the method of treatment comprises treating dysmenorrhea or fibroids through the application of a pharmaceutically acceptable composition through intravaginal administration, said pharmaceutically acceptable composition comprising a CE comprising CBD at between 75 and 99% of the total weight of the CE. In preferred embodiments, an effective amount is one effective to generate a concentration of at least 10 μg/mL of the BSHE or FSHE at the target tissue. In a further preferred embodiment, an effective dose is between 10 and 250 mg a day of CBD, wherein said CBD is provided in a BSHE or FSHE through an intravaginal application in a pharmaceutically acceptable carrier.

In certain embodiments, the CE can be administered without the need for an additional carrier. Thus, a composition suitable for administration to a patient may be the CE without any further carrier or excipient.

However, preferred embodiments include a composition for treatment of NCGD, wherein the composition comprises a *cannabis* extract (CE), wherein the CE comprises between 1 and 100% by weight of the composition and all percentages therein. In preferred embodiments, the CE comprises between 10 and 90% by weight, or 20 by 90% by weight, and preferably between 40 and 80% by weight of the composition. The CE, as detailed herein, is preferably a BSHE, a FSHE, a CBD isolate, or a CBDA isolate. In each of these different CE, the BSHE, the FSHE, the CBD isolate, or the CBDA isolate, they make up between 50 and 99.9% by weight of the CE, with the remaining being waxes, fats, fatty acids and the like. However, preferred embodiments utilize a carrier at between 1 and 99% by weight of the composition, and preferably, one or more additional excipients depending on the use case of the composition. The composition is typically then administered based upon the dosage in mg of CBD being administered. Wherein the amount of the composition required to meet that mg of CBD depends on the quantity of CBD within each of the CE.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various compositions and methods may include one or all of the limitations of an embodiment, be performed in any order, or may combine limitations from different embodiments, as would be understood by those implementing the various methods and systems detailed herein.

What is claimed is:

1. A method of treating endometriosis, symptoms associated with endometriosis, or both, the method comprising administering an effective amount of a composition to a patient, said composition comprising a carrier of between 1% and 99% by weight, said composition comprising a *cannabis* extract (CE) wherein the CE comprises cannabidiol (CBD) from about 20% to about 99.9% by weight of the CE, the CBD extracted from a Cannabaceae plant as a full spectrum hemp extract (FSHE) or a broad spectrum hemp extract (BSHE), said CE delivered within the carrier to create the composition having a pH between 3.5 and 6.

2. The method of claim 1 wherein the CE is administered to the patient as an oral form, oromucosal form, nasal form, rectal form, intravaginal form, injectable form, or combinations thereof.

3. The method of claim 1 wherein the CE further comprises cannabidiolic acid (CBDA) at a concentration of between 0.1% and 10%.

4. The method of claim 1 wherein the effective amount of CE comprises between 25 mg and 4,250 mg of CBD per dose.

5. The method of claim 1 wherein the composition comprises at least one additional compound selected from the group consisting of: a terpene, a polyphenol, an essential fatty acid, a phytonutrient, and combinations thereof; and wherein the at least one additional compound makes up between 0.1% and 50% by weight of the composition.

6. The method of claim 1 wherein the CE is administered orally using an oil or a fat as the carrier.

7. The method of claim 1 further comprising administering the CE concomitantly with a second therapeutic agent.

8. The method of claim 7 wherein the second therapeutic agent is a hormone, gonadotrophin-releasing hormone, progestin, an aromatase inhibitor, a chemotherapeutic agent, or combinations thereof.

9. The method of claim 1 wherein the CE further comprises from about 0.01% to about 0.3% by weight of $\Delta$-9-tetrahydrocannabinol ($\Delta^9$-THC).

10. The method of claim 1 wherein the CE comprises from about 70% to about 99.9% by weight of CBD.

11. The method of claim 1 wherein administering comprises administering orally up to three times per day.

* * * * *